United States Patent
Adams et al.

(10) Patent No.: US 10,053,668 B2
(45) Date of Patent: Aug. 21, 2018

(54) REPROGRAMMING BONE ENDOTHELIAL CELLS FOR USE IN BONE ANGIOGENESIS AND OSTEOGENESIS

(71) Applicant: MAX-PLANCK-GESELLSCHAFT ZUR FÖRDERUNG DER WISSENSCHAFTEN E.V., Munich (DE)

(72) Inventors: Ralf H. Adams, Münster (DE); Anjali Kusumbe, Münster (DE); Saravana Ramasamy, Münster (DE)

(73) Assignee: Max-Planck-Gesellschaft zur Föderung der Wissenschaften e.V., Munich (DE)

(*) Notice: Subject to any disclaimer, the term of this patent is extended or adjusted under 35 U.S.C. 154(b) by 0 days.

(21) Appl. No.: 15/029,186

(22) PCT Filed: Oct. 14, 2014

(86) PCT No.: PCT/EP2014/072069
§ 371 (c)(1),
(2) Date: Apr. 13, 2016

(87) PCT Pub. No.: WO2015/055688
PCT Pub. Date: Apr. 23, 2015

(65) Prior Publication Data
US 2016/0257934 A1 Sep. 8, 2016

(30) Foreign Application Priority Data

Oct. 14, 2013 (EP) ..................................... 13188509

(51) Int. Cl.
| | |
|---|---|
| C07H 21/02 | (2006.01) |
| C07H 21/04 | (2006.01) |
| C12N 5/077 | (2010.01) |
| C12N 5/071 | (2010.01) |
| C12Q 1/6881 | (2018.01) |
| G01N 33/569 | (2006.01) |

(52) U.S. Cl.
CPC ........... *C12N 5/0654* (2013.01); *C12N 5/069* (2013.01); *C12Q 1/6881* (2013.01); *G01N 33/56966* (2013.01); *C12N 2501/155* (2013.01); *C12N 2501/42* (2013.01); *C12N 2501/999* (2013.01); *C12Q 2600/158* (2013.01); *G01N 2333/70596* (2013.01)

(58) Field of Classification Search
CPC ............................. C12N 15/113; C12N 15/111
See application file for complete search history.

(56) References Cited

U.S. PATENT DOCUMENTS

| | | | |
|---|---|---|---|
| 4,816,567 A | 3/1989 | Cabilly et al. | |
| 8,227,443 B2 * | 7/2012 | MacLachlan | C12N 15/113 435/375 |

FOREIGN PATENT DOCUMENTS

WO    WO 02/09644    2/2002

OTHER PUBLICATIONS

Scherer et al. (Nat. Biotechnol., 2003, 21(12), pp. 1457-1465).*
Mahato et al. (Expert Opinion on Drug Delivery, Jan. 2005, vol. 2, No. 1, pp. 3-28).*
Sun et al. (Neuro-Oncology, 15(5), 562-577, 2013).*
Chen et al., "Noggin Suppression Decreases BMP-2-Induced Osteogenesis of Human Bone Marrow-Derived Mesenchymal Stem Cells In Vitro" Journal of Cellular Biochemistry (2012) 113(12):3672-3680.
He et al., "Interleukin-3-promotes hemangioblast development in mouse aorta-gonad-mesonephros region" Haematologica (2010) 98(6):875-883.
Köhler et al.. "Continuous cultures of fused cells secreting antibody of predefined specificity" Nature (1975) 256 (5517), 495-497.
Streeten et al., "Biology of bone endothelial cells" Bone and Mineral (Elsevier Science), 1990, 10(2):85-94.
International Search Report and Written Opinion dated Nov. 20, 2014 for PCT Application No. PCT/EP2014/072069, filed Oct. 14, 2014.
International Preliminary Report on Patentability dated Apr. 19, 2016 for PCT Application No. PCT/EP2014/072069, filed Oct. 14, 2014.
Donneys, et al., "Deferoxamine Enhances the Vascular Response of Bone Regeneration in Mandibular Distraction Osteogenesis," Plast. Reconstr. Surg. (2012) 129(4):850-856.
Qu, et al., "Promotion of osteogenesis through β-catenin signaling by desferrioxamine," Biochem. and Biophys. Res. Commun. (2008) 370:332-337.
Zou, et al., "The Bone-Forming Effects of HIF-1α-Transduced BMSCs Promote Osseointegration with Dental Implant in Canine Mandible" PLoS One (2012) 7(3):e32355.
Communication dated Jan. 4, 2017 for European Patent Application No. 14784233.0, filed Oct. 14, 2014.
Communication dated May 19, 2017 for European Patent Application No. 14784233.0, filed Oct. 14, 2014.

* cited by examiner

*Primary Examiner* — Amy H Bowman
(74) *Attorney, Agent, or Firm* — Knobbe, Martens, Olson & Bear, LLP

(57) ABSTRACT

The present invention relates to a factor for reprogramming bone endothelial cells to promote bone angiogenesis and osteogenesis as well as to an ex vivo method for reprogramming a bone endothelial cell to achieve cells able to mediate bone angiogenesis and osteogenesis. The subtype of bone endothelial cells mediating bone angiogenesis and osteogenesis express CD31 and Endomucin as markers.

11 Claims, 22 Drawing Sheets

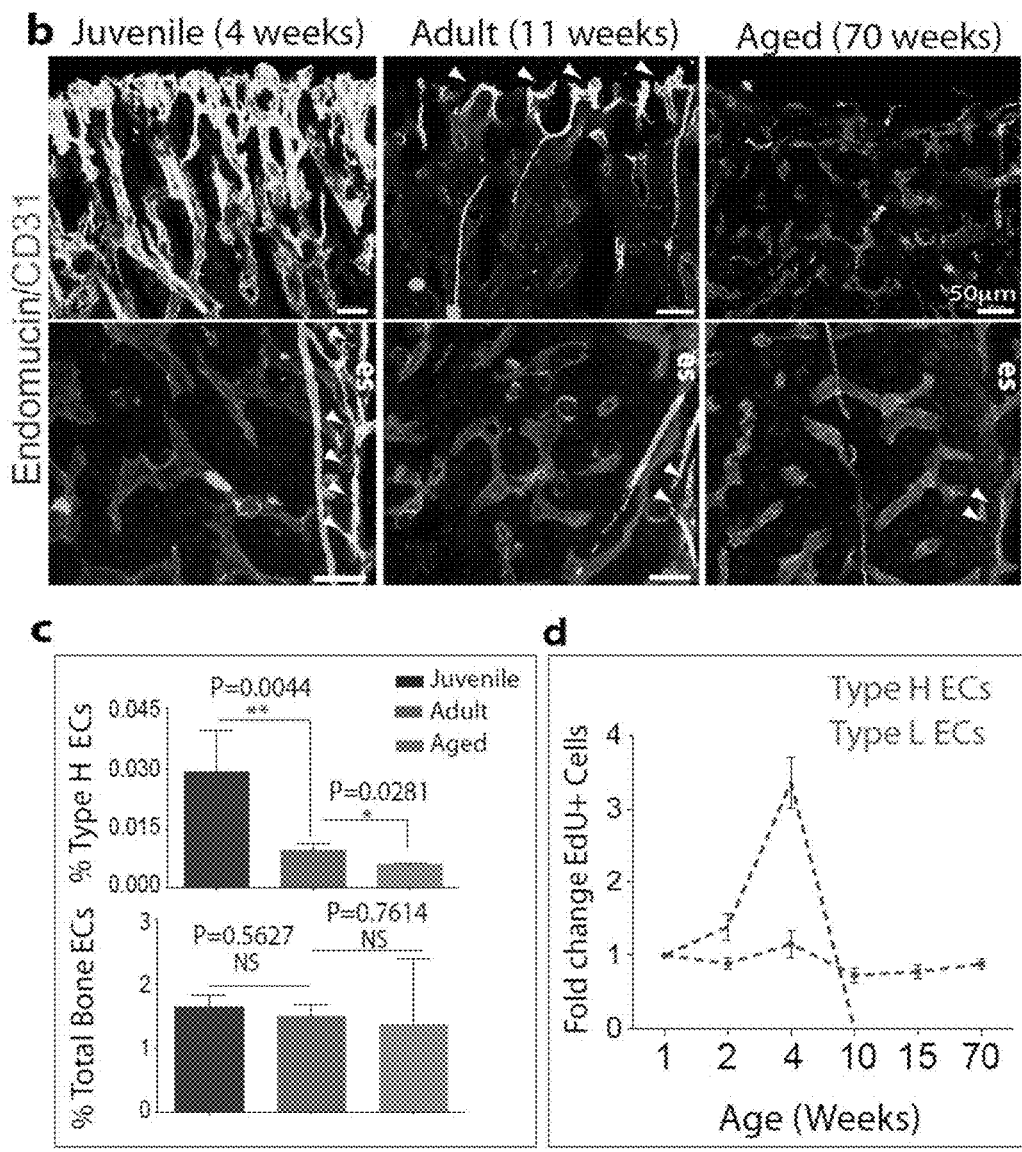
Figure 5 b – d

Figure 22

| Gene Name | Mean (hi1) | Mean (hi2) | Mean (lo1) | Mean (lo2) | Fold-Change |
|---|---|---|---|---|---|
| Stfa1 | 14,5739 | 14,8253 | 7,95934 | 6,57276 | 2,023052415 |
| H19 | 12,8743 | 13,2977 | 6,48196 | 6,47123 | 2,020506146 |
| BC100530 | 14,1083 | 14,2692 | 7,46471 | 6,60089 | 2,017510807 |
| Col18a1 | | 12,5033 | 6,40741 | 6,50804 | 1,888497884 |
| Bglap-rs1 | 13,6561 | 14,4006 | 8,55298 | 6,44023 | 1,871293739 |
| Tspan18 | 12,7729 | 13,5149 | 7,36048 | 6,97679 | 1,833522002 |
| Mest | | 12,6383 | 6,48094 | 6,8574 | 1,818404689 |
| Fbln2 | 12,0963 | 12,5861 | 7,09462 | 6,49195 | 1,816676321 |
| Cpe | 12,1051 | 12,8228 | 7,38378 | 6,47707 | 1,79843949 |
| Pxdn | 12,9787 | 13,7223 | 7,95616 | 7,08425 | 1,775284051 |
| Loxl2 | | | 6,28936 | 6,44513 | 1,771786699 |
| Alpl | | | 6,40427 | 6,56762 | 1,770890749 |
| Eml1 | | | 6,25147 | 6,47419 | 1,759099332 |
| Nes | | | 6,54734 | 6,65015 | 1,750264634 |
| Mcts2 | | | 6,20404 | 6,4415 | 1,744733716 |
| Tnnc2 | | 12,3419 | 7,03473 | 6,46283 | 1,737151011 |
| Bglap2 | | 12,5249 | 7,61262 | 6,50759 | 1,723154259 |
| Tspan18 | | | 6,25352 | 6,43735 | 1,716974486 |
| Ablim3 | 12,9804 | 13,5564 | 7,28239 | 8,36201 | 1,696249137 |
| Rbp7 | | | 6,38552 | 6,54633 | 1,689077742 |
| Plagl1 | | | 6,10563 | 6,46532 | 1,68697672 |
| Zfp521 | | | 6,30992 | 6,71028 | 1,666018955 |
| Slc39a8 | | | 6,65025 | 6,88089 | 1,664974274 |
| Vsig2 | | | 7,89213 | 6,52897 | 1,650851877 |
| Sox7 | | | 6,55297 | 6,60171 | 1,634437326 |
| Unc5b | | | 7,26272 | 6,43577 | 1,630186977 |
| Jam2 | 9,95172 | | 6,38233 | 6,45542 | 1,629531655 |
| Fxyd6 | | | 6,34115 | 7,43011 | 1,617252161 |
| Tmem98 | | | 6,36972 | 7,16848 | 1,616861917 |
| Rspo3 | | | 6,50143 | 6,54019 | 1,599264509 |
| Cyr61 | 9,69755 | | 6,39848 | 6,51954 | 1,588389707 |
| Plxna2 | | | 6,98201 | 6,39451 | 1,569900094 |
| Fkbp10 | 12,4463 | 12,6147 | 7,9676 | 8,02099 | 1,567436156 |
| Fgfr1 | | | 6,99679 | 7,45231 | 1,563370729 |
| Hey1 | | | 6,67165 | 6,50122 | 1,554019739 |
| Sparcl1 | 14,3865 | 14,7997 | | 8,49723 | 1,550492116 |
| Emcn | | | 6,52493 | 6,55429 | 1,540504709 |
| Nr2f2 | | | 7,33614 | 6,52764 | 1,536759816 |
| Apln | 9,75717 | | 6,653 | 6,8135 | 1,532133071 |
| Slco2a1 | 13,123 | 13,7867 | 8,96383 | 8,6564 | 1,527204809 |
| Madcam1 | | | 6,55372 | 7,06983 | 1,522451931 |
| Gm1673 | | | 7,29916 | 8,08218 | 1,516746915 |
| Tie1 | | | 7,52865 | 6,48316 | 1,50814206 |
| Wnt5b | | | 7,44879 | 7,52552 | 1,50080371 |
| Stfa3 | 13,7303 | 14,3326 | 8,5761 | 8,12374 | 1,50070268 |
| Sema3g | | | 7,90489 | 6,64488 | 1,500381106 |
| LOC675659 | 12,5103 | 6,72548 | 6,45522 | 6,39906 | 1,496488329 |
| Plcb4 | | | 6,51722 | 8,36247 | 1,490575408 |
| Vangl1 | | | 6,51343 | 7,87813 | 1,486371179 |
| Notch4 | 9,35896 | | 6,55114 | 6,66103 | 1,467522746 |

Figure 22 (cont.)

| Gene | Col1 | Col2 | Col3 | Col4 | Col5 |
|---|---|---|---|---|---|
| Mpp7 | 12,1924 | 7,05509 | 6,52182 | 6,61319 | 1,465357849 |
| Ehd2 | 13,4559 | 13,9042 | 9,34315 | 9,37147 | 1,461963962 |
| Flrt3 | 10,6745 | 10,2339 | 7,60027 | 6,76601 | 1,45531063 |
| Tgfb3 | 10,0621 | 10,1049 | 7,33971 | 6,66874 | 1,441073067 |
| Ltbp4 | 14,0559 | 14,5043 | 10,4606 | 9,6563 | 1,419711785 |
| Ephb4 | 13,1046 | 13,6421 | 10,1454 | 8,81842 | 1,412656428 |
| Tead2 | 11,5531 | 12,1861 | 8,4085 | 8,5153 | 1,401351942 |
| Fgfr3 | 9,84515 | 9,68109 | 7,45504 | 6,51538 | 1,397684536 |
| Dpt | 11,1495 | 7,04757 | 6,40217 | 6,87938 | 1,39036047 |
| Il13ra2 | 13,7561 | 14,1906 | 9,80953 | 10,3455 | 1,386586872 |
| Prr15 | 10,5985 | 10,7705 | 6,59528 | 8,84762 | 1,380375448 |
| Sox17 | 8,56504 | 9,41699 | 6,4274 | 6,66498 | 1,373472967 |
| Efnb1 | 11,4656 | 11,2985 | 9,07768 | 7,61381 | 1,363814734 |
| Vpreb1 | 12,5212 | 12,7439 | 8,51335 | 10,3963 | 1,343063171 |
| Flt1 | 12,7324 | 13,2905 | 10,4969 | 8,93556 | 1,339352715 |
| Tead1 | 9,00221 | 9,11767 | 6,98488 | 6,58103 | 1,335692187 |
| Bmp1 | 13,0352 | 13,305 | 10,3652 | 9,65919 | 1,315471556 |
| Sema3f | 11,7495 | 11,7507 | 9,54237 | 8,45136 | 1,301914611 |
| Cdh2 | 11,0855 | 11,1705 | 8,65965 | 8,57954 | 1,300907989 |
| Nedd4 | 12,7517 | 12,5111 | 9,10867 | 9,88325 | 1,277532761 |
| Plvap | 14,2315 | 14,6214 | 11,5928 | 11,0434 | 1,276326848 |
| Cd34 | 14,4088 | 14,8137 | 11,4719 | 11,5186 | 1,271068485 |
| Vegfa | 8,50084 | 8,45656 | 6,44863 | 7,8803 | 1,183437982 |

REPROGRAMMING BONE ENDOTHELIAL CELLS FOR USE IN BONE ANGIOGENESIS AND OSTEOGENESIS

The present invention relates to a factor for reprogramming bone endothelial cells to promote bone angiogenesis and osteogenesis as well as to an ex vivo method for reprogramming a bone endothelial cell to achieve cells able to mediate bone angiogenesis and osteogenesis. The subtype of bone endothelial cells mediating bone angiogenesis and osteogenesis express CD31 and Endomucin as cell surface markers.

BACKGROUND OF THE INVENTION

Bone is in a constant state of flux, being built up by bone-forming cells called osteoblasts while also being broken down or resorbed by cells known as osteoclasts. Osteoblasts arise from osteoprogenitor cells located in the deeper layer of periosteum and the bone marrow. Osteoprogenitors are immature progenitor cells that express the master regulatory transcription factor Cbfa1/Runx2. Osteoprogenitors are induced to differentiate under the influence of growth factors. Once osteoprogenitors start to differentiate into osteoblasts, they begin to express a range of genetic markers including Osterix.

During childhood and adolescence, bone formation is dominant; bone length and width increase with age, ending at early adulthood when peak bone mass is attained. At some age, the rate of bone resorption in humans starts to exceed the rate of bone formation. Women experience additionally accelerated bone loss after menopause, when the estrogen level decreases.

Osteoporosis is a progressive bone disease that is characterized by a decrease in bone mass and density and that leads to an increased risk of fracture. Osteoporosis occurs primarily as a result of normal aging, but can arise as a result of impaired development of peak bone mass or excessive bone loss during adulthood. Factures induced by osteoporosis are a great burden to society. Hip fractures are the most serious, as they nearly always result in hospitalization. According to the WHO fracture rates increase rapidly with age and the lifetime risk of fracture in 50 year-old women is about 40%, similar to that for coronary heart disease. In 1990, there were 1.7 million hip fractures alone worldwide; with changes in population demographics, this figure is expected to rise to 6 million by 2050.

Therefore there is an urgent need to provide factors effectively mediating bone angiogenesis and osteogenesis. The term "osteogenesis" or "ossification" as used herein refers to bone tissue formation. There are two types of ossification resulting in the formation of normal, healthy bone tissue. Intramembranous ossification is the direct laying down of bone into the primitive connective tissue (mesenchyme) occurring along a template of membrane. It results primarily in compact flat bones of the skull. During endochondral ossification mineral salts calcify along the scaffolding of cartilage used as a precursor. During embryogenesis the primary center of ossification, the diaphysis of the long bone is the first to form spongy bone tissue along the cartilage, followed by the epiphyses, which form the secondary centers of ossification and are separated from the diaphysis by a layer of uncalcified cartilage called the epiphyseal plate, where growth in bone length occurs. Compact bone tissue covering the bone's surface is produced by osteoblasts in the inner layer of the periosteum, producing growth in diameter. In fracture healing, endochondral osteogenesis is the most commonly occurring process.

It is the objective of the present invention to provide compounds or factors mediating bone angiogenesis and osteogenesis, which can be used as pharmaceutically active agents, especially for use in the treatment of osteoporosis or promotion of bone fracture healing.

The objective of the present invention is solved by the teaching of the independent claims. Further advantageous features, aspects and details of the invention are evident from the dependent claims, the description, the figures, and the examples of the present application.

DESCRIPTION OF THE INVENTION

Osteogenesis is indispensable for the homeostatic renewal of bone as well as regenerative fracture healing, but these processes frequently decline in aging organisms leading to loss of bone mass and increased fracture incidence. There is evidence indicating that the growth of blood vessels in bone and osteogenesis are coupled. The inventors could identify a new capillary subtype in the skeletal system with distinct morphological, molecular and functional properties. These vessels, herein also named type H capillaries, are found in specific locations, mediate growth of the bone vasculature, generate distinct metabolic molecular microenvironments, maintain perivascular osteoprogenitors, and couple angiogenesis to osteogenesis. The abundance of these vessels and associated osteoprogenitors is strongly reduced in bone from aged animals, which was pharmacologically reversible to restore bone mass.

Therefore it is feasible to use a factor suitable for reprogramming any other type of endothelial cell into type H endothelial cells for use in the treatment of conditions where bone angiogenesis and osteogenesis is desired. By application of said factor generation of type H endothelial cells is mediated. Thereby a transition of cells into type H endothelial cells takes place resulting in an increased amount of vessels able to promote angiogenesis and osteogenesis. A factor or compound which is able to increase the amount of type H endothelial cells would be suitable for the treatment of osteoporosis or for promotion of bone fracture healing. Thus the present invention relates to a factor suitable for generating type H bone endothelial cells for use in promoting bone angiogenesis and osteogenesis.

The endothelial cells of this type of capillaries, called type H bone endothelial cells, were strongly positive for the markers CD31/PECAM1 and Endomucin (Emcn). As these $CD31^{hi}/Emcn^{hi}$ capillaries are found at the distal end of the arterial network in bone, they are the central building block of a metabolically specialised tissue environment with privileged access to oxygen and nutrients. Furthermore the data of the inventors suggest that these will influence the growth potential and behaviour of cell types surrounding the vasculature. This is particularly relevant for osteoblastic cells. It has further been found that the new type of endothelial cells mediate local growth of the vasculature and provide niche signals, such as secreted growth factors, for perivascular osteoprogenitors. The type H endothelial cells having these particular characteristic constitute only a very small subpopulation of endothelial cells (in an adult mouse <2%). Thereby a type H bone endothelial cell shows at least a four fold increased expression of CD31 and a two fold increased expression of Emcn, compared to the basal level of a L type bone endothelial cell, both to protein and transcript level.

Type H bone endothelial cells are further characterized by a specific expression profile as shown in table 2.

The present invention relates further to a factor for reprogramming type L) (CD31$^{lo}$/Emcn$^{lo}$ bone endothelial cells to type H (CD31$^{hi}$/Emcn$^{hi}$) bone endothelial cells for use in promoting bone angiogenesis and osteogenesis.

In developmental biology, cellular differentiation is the process by which a less specialized cell becomes a more specialized cell type. Differentiation dramatically changes a cell's size, shape, membrane potential, metabolic activity, and responsiveness to signals. These changes are largely due to highly controlled modifications in gene expression. With a few exceptions, cellular differentiation almost never involves a change in the DNA sequence itself. Thus, different cells can have very different physical characteristics despite having the same genome.

"Reprogramming" as used herein refers to a change in cell differentiation and is thus a transition of a cell, especially an endothelial cell from one cell type, here type L) (CD31$^{lo}$/Emcn$^{lo}$ bone endothelial cells to another, type H (CD31$^{hi}$/Emcn$^{hi}$) bone endothelial cells, and it involves a switch from one pattern of gene expression to another.

Since each cell of a body, regardless of cell type, possesses the same genome, determination of cell type must occur at the level of gene expression. The regulation of gene expression can occur through regulatory elements in the genome, like promoter sequences and enhancers, an expression pattern is maintained over several generations of cell division by epigenetic processes like alterations in chromatin structure including DNA methylation.

Also cell signaling is able to influence epigenetic processes governing differentiation, so that extrinsic signaling can lead to epigenetic remodeling, just as it can lead to changes in gene expression through the activation or repression of different transcription factors.

Reprogramming can also be induced artificially through the introduction of exogenous factors, usually transcription factors but also by introducing factors interfering with the signaling pathways mediating reprogramming of a cell.

The reprogramming of type L bone endothelial cells to type H bone endothelial cells for bone angiogenesis and osteogenesis according to the invention may be done "in situ" or "in vivo" by administering the factor to a patient but may also be done "in vitro" by isolating type L bone endothelial cells, reprogramming them under cell culture conditions and re-transplanting the reprogrammed type H bone endothelial cells locally for promoting bone fracture healing or bone formation in general.

The isolated type L bone endothelial cells can be taken from any bone within an organism and are preferably derived from a mammal, like a mouse or a human. The mammal may be an adult, a juvenile or a fetus. The type L bone endothelial cell should be isolated as a primary cell. When the type H bone endothelial cell produced by the use of the factor according to the present invention is used for the treatment of a patient, it is preferred to use cells which have been isolated from the patient himself (autologous transplantation).

The reprogramming factor according to the invention is suitable for use in the prophylaxis and the treatment of osteoporosis or for use in promotion of bone fracture healing or in general for use in the treatment of disease conditions where endogenous bone formation is defective or insufficient.

A factor or compound according to the invention may be selected from:

(i) nucleic acids, in particular small interfering RNA (sRNA), micro RNA (miRNA) or a precursor thereof, oligonucleotide aptamers, anti-sense oligonucleotides, or ribozymes;
(ii) peptidic compounds, in particular proteins, like signaling molecules, antibodies or antibody fragments or peptidic aptamers;
(iii) small organic non-peptidic molecules, i.e. molecules having a low molecular weight; and
(iv) combinations thereof.

Such a factor or compound may have the ability to mediate or promote programming of bone endothelial cells into a state that supports vessel growth and bone formation.

Such factors or compounds may have the ability to specifically reprogram bone endothelial cells, e.g. due to nuclear reprogramming an endothelial cell (e.g. by altering the particular pattern of regulated gene expression for example through chromatin remodeling).

In one embodiment, the reprogramming factor is able to bind a target polypeptide, i.e. a factor acting on the protein level. A factor able to bind a target polypeptide, i.e. factor acting on protein level, may be a peptide acting as a ligand on a receptor and thereby activating or inhibiting a specific signaling pathway, like Notch pathway.

A factor able to bind a target polypeptide, i.e. factor acting on protein level, may also be an antibody inactivating the target polypeptide. In the context of the present invention, the term "antibody" covers monoclonal antibodies, polyclonal antibodies, multispecific antibodies (e.g. bispecific antibodies) formed from at least two antibodies, antibody fragments and derivatives thereof as long as they exhibit the desired activity. The antibody may be an IgM, IgG, e.g. IgG1, IgG2, IgG3 or IgG4. Antibody fragments comprise a portion of an antibody, generally the antigen binding or variable region of the intact antibody. Examples of antibody fragments include Fab, Fab', F (ab') 2 and Fv fragments, diabodies, single chain antibody molecules and multispecific antibody fragments.

Particularly, the antibody may be a recombinant antibody or antibody fragment, more particularly selected from chimeric antibodies or fragments thereof and diabodies. For therapeutic purposes, particularly for the treatment of humans, the administration of chimeric antibodies, humanized antibodies or human antibodies is especially preferred. A monoclonal antibody may be obtained by the hybridoma method as described by Köhler et al. (Nature 256 (1975), 495) or by recombinant DNA methods (cf. e.g. U.S. Pat. No. 4,816,567). Monoclonal antibodies may also be isolated from phage antibody libraries using techniques which are known to the person skilled in the art.

A reprogramming factor able to bind a target polypeptide, i.e. factor acting on protein level, may be an aptamer, i.e. an oligonucleic acid, a peptide molecule or a combination thereof that specifically binds to a target polypeptide. An oligonucleic acid aptamer may have a sequence length of about 20-100 nucleotides, preferably about 25-75, more preferably about 30-50 nucleotides. A peptide aptamer generally consists of a variable peptide loop attached at both ends to a protein scaffold. The variable loop length is between 5 and 50, preferably about 10-30, and more preferably about 10-20 amino acids. Aptamers are mostly short single stranded DNA- or RNA-molecules, which can bind a specific molecule because of their 3D-structure. Aptamers may be prepared by chemical synthesis as known by the person skilled in the art.

Further, the reprogramming factor may be a small organic non-peptidic molecule. Such a molecule has a low molecular weight between 100 and 1000 g·mol$^{-1}$ and preferred between 300 and 500 g·mol$^{-1}$. Said molecule may act as an inhibitor of an enzymatic activity, e.g. a prolyl-4-hydroxylase. The term small molecule refers to low molecular weight organic compound which is by definition not a polymer. In the field of pharmacology, it is usually restricted to a molecule that also binds with high affinity to a biopolymer such as proteins, nucleic acids, or polysaccharides. Small molecules are broadly used as enzyme inhibitors.

In a further embodiment, the factor according to the invention is directed against a target nucleic acid, i.e. factor acting on the nucleic acid level. Preferably, the factor is a nucleic acid compound, e.g. RNAi inducing molecules like sRNA, miRNA, anti-sense oligonucleotide, ribozyme, a precursor or a combination thereof.

A RNAi-inducing molecule may refer to a nucleic acid molecule, wherein at least one polynucleotide strand of said nucleic acid molecule has a sequence which is sufficiently complementary to a target RNA, preferably to a target mRNA, in order to effect its processing, i.e. its decomposition. In order to have an RNAi-inducing effect, it is necessary that the complementarity between the RNAi-inducing molecule and a region of the target RNA is sufficient, in order to effect a hybridization and a subsequent processing. For example, the complementarity is at least 80%, preferably at least 90% and most preferably at least 99%, whereby the 5'-and/or 3'-ends as well as the overhangs of an RNAi-effector molecule may also contain nucleotides which are not complementary to the target RNA.

SiRNA (small interfering RNA or short interfering RNA or silencing RNA) used according to the invention is a double-strand of RNA and/or nucleotide analogues with 3' overhangs on at least one end, preferably either ends. Each RNA strand of the double-strand has a 5' phosphate group and a 3' hydroxyl group. Preferably, each RNA strand of the double strand is 19 to 30 nucleotides long, more preferably 20 to 28 nucleotides and most preferably 21 to 23 nucleotides. In a particular preferred embodiment the siRNA double-strand consists of two 21 nucleotides long RNA strands each having a 3' overhang. SiRNA molecules further refer to single-stranded RNA-molecules having a length of 19-30 nucleotides, preferably 20-28 nucleotides and particularly having a length of 21-23 nucleotides, whereby the single-stranded RNA molecule is for at least 80%, preferably for at least 90% and more preferably for more than 99% complementary to a sequence of a target RNA, in particular of a target mRNA, and a binding of siRNA to the target RNA effects a sequence specific decrease. Preferably, siRNA molecules have overhangs of 1-3 nucleotides on the 3' end. Methods for obtaining siRNA molecules are known to the person skilled in the art.

MiRNA is a single- or double-stranded RNA molecule of 19-30, preferably 20-28, and more preferably 21-23 nucleotides in length, which can regulate gene expression. MiRNA is generally synthesized at first as a precursor, which is then processed to the major form having a sequence which is at least partially complementary to messenger RNA of a target molecule according to the invention.

An antisense oligonucleotide may be a single, double, or triple-stranded DNA, RNA, PNA (peptide nucleic acid) or a combination thereof (e.g. hybrids of DNA and RNA strands) having a length of between about 10-100, preferably 20-50, and more preferably 20-30 nucleotides in length, which can interfere with mRNA targets by hybrid formation and therefore inhibit translation of said mRNA.

Ribozymes are catalytic RNAs which possess a well defined structure that enables them to catalyze a chemical reaction. Apart from naturally occurring ribozymes they can be made artificially and be tailored to interact with nucleic acids and proteins. Ribozymes are also preferred factors for inhibition of the preferred kinases in the present invention.

Precursor molecules, e.g. precursor molecules of siRNA and/or miRNA may be a substrate for the siRNA/miRNA-biogenesis-apparatus of the target cell. This comprises, for example, RNA precursor molecules such as double-stranded RNA (dsRNA) or short hairpin RNA-molecules (shRNA), which are processed by enodribonucleases such as Drosha and/or Pasha to siRNA-molecules or miRNA-molecules, respectively. Dicer is another endoribonuclease that cleaves double-stranded RNA and pre-microRNA (miRNA) into siRNA about 20-25 nucleotides long, usually with a two-base overhang on the 3' end. Dicer catalyzes the first step in the RNA interference pathway and initiates formation of the RNA-induced silencing complex (RISC). The RISC complex with a bound siRNA recognizes complementary messenger RNA (mRNA) molecules and degrades them, resulting in substantially decreased levels of protein translation and effectively turning off the gene.

DsRNA-molecules or short hairpin RNA-molecules (shRNA) having a length of more than 27 nucleotides, preferably more than 30 up to 100 nucleotides or longer, and mostly preferred dsRNA-molecules having a length of 30-50 nucleotides, can be used.

Further precursor molecules according to the invention may be DNA constructs encoding dsRNA, shRNA, siRNA and/or miRNA, whereby the coding elements are controlled by regulatory elements allowing an expression of dsRNA, shRNA, siRNA and/or miRNA in the target cell. Examples for such control elements are polymerase II promoters or polymerase III promoters such as, for example, U6 or H1.

SiRNA, miRNA, ribozymes and antisense oligonucleotides may be coupled with a labeling group, e.g. for diagnostic purposes or may be coupled with an effector molecule known in the art and they may be applied to a target cell by any technique which is known to a person skilled in the art, such as transfection of exogenous siRNA, miRNA, ribozyme and antisense oligonucleotide or of an appropriate vector, e.g. viral or non-viral, producing a single transcript which can be processed into a functional siRNA, miRNA, ribozyme or antisense oligonucleotide.

In another embodiment of the invention, the factor is a nucleic acid having reprogramming activity. Such a nucleic acid can be isolated by methods known to a skilled person and used to recombinantly express proteins encoded by said nucleic acids. The nucleic acid can be used for transfecting cells which are destined to be reprogrammed. For the purpose of overexpression in endothelial bone cells the nucleic acid can be placed in expression vectors capable of expressing an encoded protein, polypeptide or peptide. Nucleic acids encoding a desired protein or polypeptide may be derived from cDNA or genomic clones using conventional methods and subsequently ligated into expression vectors. Therefore the present invention is also directed to a recombinant DNA-molecule and an expression vector which includes a DNA-molecule displaying reprogramming activity generating type H bone endothelial cells.

The findings of the inventors highlight crucial roles of endothelial HIF in the regulation of bone angiogenesis, the abundance of type H vessels, the expression of secreted growth factors by endothelial cells, and osteogenesis. Hypoxia-inducible factors (HIFs) are transcription factors that respond to changes in available oxygen in the cellular environment, specifically, to decreases in oxygen, or hypoxia. HIF1 is a heterodimeric basic helix-loop-helix structure composed of HIF-1α, the alpha subunit, and the aryl hydrocarbon receptor nuclear translocator (Arnt), the beta subunit.

Thus in one preferred embodiment a factor or compound of the present invention has the ability to increases the stability or biological activity of HIF-1 α. Thus, suitable factors according to the invention are active HIF-1alpha or factors inhibiting VHL (van Hippel-Lindau) or E3 ubiquitin protein ligase (see also FIGS. 6d and 7a).

Prolyl-4-hydroxylases (PHDs) modify HIF-1α and thereby mark the protein for degradation under normoxic conditions. Accordingly, administration of PHD inhibitors such as deferoxamine mesylate (DFM) enhances HIF-1α stability and activity. Therefore one embodiment of the present invention refers to prolyl-4-hydroxylase inhibitor as factor for reprogramming type L bone endothelial cells to type H bone endothelial cells mediating bone angiogenesis and osteogenesis and especially for use in the treatment of osteoporosis or promotion of bone fracture healing. Thus preferred factors of the present invention are prolyl-4-hydroxylase inhibitors. Preferred PHD inhibitors are selected from the group comprising or consisting of: cobalt chloride, ciclopirox olamine (both are iron chelators), L-mimosine, dimethyloxalylglycine (DMOG), 3,4-dihydoxybenzoate (these three compounds compete for endogenous 2-oxoglutarate) and (N'-{5-[Acetyl(hydroxy)amino]pentyl}-N-[5-({4-[(5-aminopentyl)(hydroxy)amino]-4-oxobutanoyl}amino)pentyl]-N-hydroxysuccin amide). According to the invention, deferoxamine mesylate (N'-{5-[Acetyl(hydroxy)amino]pentyl}-N-[5-({4-[(5-aminopentyl)(hydroxy)amino]-4-oxobutan oyl}amino)pentyl]-N-hydroxysuccinamide) is particularly preferred.

The Notch pathway is an important negative regulator of angiogenesis in many model systems (zebrafish, mouse). Thereby Notch and its ligand Delta-like 4 (Dll4) suppress excessive tip cell formation and proliferation in growing vasculature. Surprisingly and opposite of the well-established function of Notch it has been found that in tissue specific form of angiogenesis in bone Notch signalling promotes endothelial cell proliferation and vascular growth. It has been shown that administration of noggin, which acts downstream of Notch, restores bone growth and mineralization as well as osteoprogenitor and osteoblast numbers in endothelial cell-specific Notch pathway mouse mutants.

Thus in one preferred embodiment a reprogramming factor or compound of the present invention activates Notch-signaling. Factors according to the invention activating Notch-signaling may be an immobilized Dll4/Fc fusion protein, the activated intracellular domaine of Notch (see FIG. 17) or a factor inactivating an enzyme able to destruct active Notch, such as Fbxw7 (see FIG. 15 as well as 16j and n). Preferably, the factor according to the present application is not noggin.

Another aspect of the present invention refers to the use of a factor increasing the stability or biological activity of HIF-1α or activating Notch-signaling for the manufacture of a medicament for use in the treatment of osteoporosis or promotion of bone fracture healing.

For use in medicine or as a medicament, the reprogramming factor or a combination of more than one factor according to the invention may be formulated as a pharmaceutical composition. Thus, another aspect of the present invention is directed to pharmaceutical compositions comprising at least one factor of the present invention as active ingredient, together with at least one pharmaceutically acceptable carrier, excipient and/or diluent. The pharmaceutical compositions of the present invention can be prepared in a conventional solid or liquid carrier or diluent at suitable dosage level in a known way. The preferred preparations are adapted for oral application. These administration forms include, for example, pills, tablets, film tablets, coated tablets, capsules, powders and deposits. Another preferred preparation is adapted for injection. By injection the factor may be applied to the target side nearby or in the bone having a fracture.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one factor according to the present invention as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the factor increasing the stability or biological activity of HIF-1α or activating Notch-signaling as active ingredient.

Suitable binders include starch, gelatin, natural carbohydrates, corn sweeteners, natural and synthetic gums such as acacia, sodium alginate, carboxymethylcellulose, polyethylene glycol and waxes. Among suitable lubricants, there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the factors or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices. Suitable dosage forms for sustained release include furthermore implants releasing a factor of the present application coated thereon.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The factors according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticizers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include carbohydrates such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances, which bind or "glue" together powder particles and make them cohesive by forming granules, thus serving as the "adhesive" in the formulation. Binders add cohesive strength already available in the diluent or bulking agent. Suitable binders include carbohydrates such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The mentioned pharmaceutical formulations are characterized in that they comprise a factor inducing reprogramming type L bone endothelial cells to type H bone endothelial cells mediating bone angiogenesis and osteogenesis and preferably a factor increasing the stability or biological activity of HIF-1α or interfering with Notch-signaling.

The factors of the invention are present in said pharmaceutical formulation in the range of 1 to 1000 μg/g. In a preferred embodiment of the invention the factors are present in said formulation in the range of 10 to 1000 ng/g.

When applied in vivo the factors of the present invention were found of being capable of effectively reprogramming cells, especially type L endothelial cells or $CD31^{lo}/Emcn^{lo}$ bone endothelial cells to form type H endothelial cells or $CD31^{hi}/Emcn^{hi}$ bone endothelial cells. This is rather advantageous, since the induced type of endothelial cells build vessels which are found in specific locations, mediate growth of the bone vasculature, generate distinct metabolic and molecular microenvironments, maintain perivascular osteoprogenitors, and couple angiogenesis to osteogenesis. Therefore these cells promote restoring of bone mass.

One aspect of the present invention refers to an ex vivo method for generating type H bone endothelial cells comprising the step of:

contacting an isolated cell with a factor that contributes to reprogramming of said cell to type H endothelial cell.

Thereby an isolated cell is preferably an endothelial cell and particularly a type L bone endothelial cell. Furthermore the isolated cell may be a cell of a primary cell culture derived from a human or animal or it may be an immortalized cell of a cell culture clone. Deriving such an isolated cell can be done by standarized techniques known in the art. One example for isolation and culture of endothelial cells from bone (tibiae and femurs from wild-type mice) is described in the examples of the present disclosure.

Further aspect of the present invention refers to an ex vivo method for generating type H bone endothelial cells comprising the steps of:
a) providing an isolated cell and
b) contacting said isolated cell with a factor that contributes to reprogramming of said cell to type H endothelial cell.

Thereby cellular reprogramming of a somatic cell into type H endothelial cell takes place. The isolated cell can represent each fully differentiated, specialized cell type apart from type H endothelial cell. Without contact to said factor and under normal physiological conditions the isolated cell would not become a type H endothelial cell. It is preferred that the isolated cell is an endothelial cell, especially a type L cell or $CD31^{lo}/Emcn^{lo}$ bone endothelial cell.

A yet another aspect of the present invention refers to a method of reprogramming type L bone endothelial cells to type H bone endothelial in a human and/or animal comprising administering to the human and/or animal host, the factor or pharmaceutical composition of the invention. Thereby the present invention refers preferably to a method for the treatment of a patient suffering from osteoporosis or having a bone fracture comprising administering to the patient a factor increasing the stability or biological activity of HIF-1α or interfering, preferably activating, Notch-signaling.

Furthermore the present invention refers to a method for isolating bone endothelial cells able to mediate bone angiogenesis and osteogenesis. This method may comprise isolation of cells and preferably only endothelial cells from fresh bone tissues. Subsequently the bone endothelial cells able to mediate bone angiogenesis and osteogenesis may be labeled with antibodies against the surface markers CD31 and Emcn and separated from the remainder of the cells and debris by capture with magnetic beads or by high-speed cell sorting.

Especially for screening and identification of novel drugs it could be suitable to reprogram isolated endothelial cells ex vivo which means in cell culture. Furthermore it is possible to re-transplant isolated and reprogrammed cells to a patient.

Another aspect of the present invention is therefore directed to an ex vivo or in vitro method for reprogramming a type L bone endothelial cell to a type H endothelial cell comprising the step of:
contacting an isolated cell with a factor that contributes to reprogramming of said cell to a type H endothelial cell.

Another aspect of the present invention is therefore directed to an ex vivo or in vitro method for reprogramming a type L bone endothelial cell to a type H endothelial cell comprising the steps of:
a) providing an isolated type L bone endothelial cell and
b) contacting said isolated cell with a factor that contributes to reprogramming of said cell to a type H endothelial cell.

As used herein "contacting" means bringing the isolated cell and the factor in contact, namely under time, medium and temperature conditions sufficient to begin the reprogramming process. In this respect, contacting may also be referred to "incubating".

Thus the above mentioned methods comprise preferably a third step, namely:
c) maintaining said cell under conditions appropriate for proliferation of said cell and activity of the factor.

Another embodiment of the present invention refers to an ex vivo or in vitro method for reprogramming a type L bone endothelial cell to a type H endothelial cell comprising the steps of:
a) providing an isolated type L bone endothelial cell and
b) increasing the stability or biological activity of HIF-1α in said isolated cell or
b)' activating Notch-signaling in said isolated cell.

Step b) or b)' are carried out by contacting said isolated cell with a factor able to increase the stability or biological activity of HIF-1α or to activate Notch-signaling in said isolated cell, respectively.

Cell culture conditions sufficient to begin the reprogramming process are same normal conditions as those for culturing primary endothelial cells which include culture of the cells on fibronectin coated dishes in endothelial cell growth medium (EBM-2, Clonetics; Lonza) supplemented with EGM-2 SingleQuots (CC-4176, Clonetics; Lonza) and were maintained at 37° C. with 5% $CO_2$ in a humidified atmosphere. Reprogramming process of these endothelial cells beings within 1 day in presence of a factor according to the invention (for example Hif1α stabilisator) and can be achieved completely within 2 to 5 days.

The inventors could show that bone angiogenesis is mediated by vessel columns and arches, which are highly distinct from growing vasculature in other tissues. These vessels in the metaphysis are strongly positive for the markers CD31/PECAM1 and Endomucin (Emcn), while the irregular, sinusoidal vessels in the diaphysis displayed substantially lower expression of CD31 and Endomucin. The comparison of different immunostainings showed that it is possible to distinguish the specific vessel type or capillary subset with the cell surface marker CD31/PECAM1 and Endomucin (Emcn). These findings not only apply to long bones, but also to other such as vertebra and sternum. The analysis of endothelial cells from other organs showed that they all, with the exception of liver, lack a comparable type H capillary subset.

Therefore, the present invention refers further to use of CD31 and Endomucin as marker for type H bone endothelial cells, which are able to mediate growth of bone vasculature. This method regards preferably to ex vivo usage. Common methods wherein such markers are used are e.g. labeling of isolated cells or cells in tissue samples and visualization in flow cytometry or fluorescence microscopy. The subtype of bone endothelial cells, CD31 and Endomucin are suitable markers for, mediate bone angiogenesis and maintain perivascular osteoprogenitors. These markers may be used for assessment of the endogenous state of the bone vasculature in different diseases conditions, preferably at isolated tissue or cell samples. Furthermore they are useful for development and identification of novel pharmaceutical active agents controlling or interfering with the programming of bone endothelial cells.

Platelet endothelial cell adhesion molecule (PECAM-1) also known as cluster of differentiation 31 (CD31) is a protein that in human is encoded by the PECAM1 gene found on chromosome 17. CD31 is found on endothelial cells, platelets, macrophages and Kupffer cells, granulocytes, T/NK cells, lymphocytes, megakaryocytes, osteoclasts, and neutrophils. Endomucin is a protein that in humans is encoded by the EMCN gene. Endomucin is a mucin-like sialoglycoprotein that interferes with the assembly of focal adhesion complexes and inhibits interaction between cells and the extracellular matrix.

TABLE 1

Sequence identities of the marker genes and marker proteins

| SeqIdNo | Sequence Name | Gene ID/Acession No. NCBI |
|---|---|---|
| 1 | CD31 gene mouse | 18613 |
| 2 | EMCN gene mouse | 59308 |
| 3 | CD31 protein mouse | NP_032842.2/ NP_001027550.1 |
| 4 | Endomucin protein mouse | AAD05208.1 |
| 5 | CD31 gene human | 5175 |
| 6 | EMCN gene human | 51705 |
| 7 | CD31 protein human | NP_000433.4 |
| 8 | Endomucin protein human | AAF76295.1 |

Another embodiment of the present invention is a bone endothelial cell obtained according to any method described herein. Thus the present invention refers to an isolated type H bone endothelial cell as well as to type H bone endothelial cell obtained by reprogramming. These cells are characterized by highly expressing CD31 and Emcn and by their ability to mediate growth of bone vasculature and maintain perivascular osteoprogenitors.

The invention refers furthermore to a screening method for the purpose of identifying reprogramming factors according to the invention comprising the following steps:
  contacting bone endothelial cells with a candidate compound and
  detecting the expression of the marker proteins CD31 and Endomucin in these cells.

Another aspect of the present invention refers to a method of determining a subtype of bone endothelial cells mediating growth of bone vasculature, comprising:
  measuring the expression level CD31 and Endomucin in a bone endothelial cell, wherein an increased CD31 and Endomucin expression level is indicative for the subtype of bone endothelial cells mediating growth of bone vasculature.

In regard to the method according to the present invention it is preferred if the expression level of CD31 and Endomucin is increased in said specific endothelial cells at least 1.5-fold, preferred at least 2-fold and more preferably at least 4-fold compared to the expression level in other types of endothelial cells from said subject.

Increasing the amount of type H endothelial cells by application of the reprogramming factors of the present invention leads to an improved osteogenesis which could be important in elderly people and during fracture healing.

The method of determining a subtype of bone endothelial cells according to the present invention refers to determination of the expression of CD31 and Endomucin on the protein level, or of the expression of CD31 and Endomucin on the nucleic acid level. Thereby the expression level between different samples, e.g. between different endothelial cells isolated from bone vasculature or samples at different time of treatment, are compared.

Gene expression is the process by which information from a gene is used in the synthesis of a functional gene product. These products are often proteins, but in non-protein coding genes such as rRNA genes or tRNA genes, the product is a functional RNA. Several steps in the gene expression process may be modulated, including the transcription, RNA splicing, translation, and post-translational modification of a protein.

The expression level of genes can be determined on the nucleic acid level, preferably on the level of mRNA. Levels of mRNA can be quantitatively measured by Northern blotting. A sample of RNA is separated on an agarose gel and hybridized to a labeled RNA probe that is complementary to the target sequence. The labeled RNA is then detected. Alternatively the level of mRNA can be measured by reverse transcription quantitative polymerase chain reaction (RT-PCR followed with qPCR) to compare mRNA abundance between samples, e.g. between a cancer and a non-malignant cell sample.

RT-PCR first generates a DNA template from the mRNA by reverse transcription, which is called cDNA. This cDNA template is then used for qPCR where the change in fluorescence of a probe changes as the DNA amplification process progresses. With a carefully constructed standard curve qPCR can produce an absolute measurement such as number of copies of mRNA. Relative concentrations of DNA present during the exponential phase of the reaction may be determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, Ct. The quantity of DNA theoretically doubles every cycle during the exponential phase and relative amounts of DNA can be calculated, e.g. a sample whose Ct is 3 cycles earlier than another's has $2^3=8$ times more template. Since all sets of primers don't work equally well, one has to calculate the reaction efficiency first. Thus, by using this as the base and the cycle difference C(t) as the exponent, the precise difference in starting template can be calculated (in previous example, if efficiency was 1.96, then the sample would have 7.53 times more template).

Amounts of DNA are then determined by comparing the results to a standard curve produced by real-time PCR of serial dilutions (e.g. undiluted, 1:4, 1:16, 1:64) of a known amount of DNA. To accurately quantify gene expression, the measured amount of DNA from the gene of interest is divided by the amount of DNA from a housekeeping gene measured in the same sample to normalize for possible variation in the amount and quality of DNA between different samples e.g. between a cancer and a non-malignant cell sample. This normalization permits accurate comparison of expression of the gene of interest between different samples, provided that the expression of the reference (housekeeping) gene used in the normalization is very similar across all the samples. Additionally "tag based" technologies like Serial analysis of gene expression (SAGE), which can provide a relative measure of the cellular concentration of different messenger RNAs, can be used.

The expression of genes on the protein level may be detected by a Western blot. Thereby a sample is separated on a polyacrylamide gel, transferred to a membrane and then probed with an antibody to the protein of interest. The antibody can either be conjugated to a fluorophore or to horseradish peroxidase for imaging and/or quantification.

Alternatively an enzyme-linked immunosorbent assay (ELISA) may be used which works by using antibodies immobilised on a microtiter plate to capture proteins of interest from samples added to the well. Using a detection antibody conjugated to an enzyme or fluorophore the quantity of bound protein can be accurately measured by fluorometric or colorimetric detection.

In mass spectrometry-based methods relative quantification is possible to compare protein abundance between samples, e.g. between a cancer and a non-malignant cell sample. This can be achieved by labeling one sample with stable isotopes alone or incorporated into protein cross-linkers, which leads to a mass shift in the mass spectrum. Differentially labeled samples are combined and analyzed together. The differences in the peak intensities of the isotope pairs accurately reflect difference in the abundance of the corresponding proteins.

b, Organisation and osteogenic role of growing vessels in the postnatal metaphysis of long bone. Endothelial columns, which are embedded between segments of forming trabecular bone, are interconnected by arches at their distal end. Blind-ended, lumen-containing protrusions extend from arches towards growth plate chondrocytes, a known source of VEGF. Endothelial Notch signaling promotes endothelial proliferation and vessel growth in bone, which is the opposite of its role in other tissues. Notch activity in ECs is also required for endothelial Noggin expression, which controls perivascular osteoprogenitor cells and thereby the formation of new bone in an angiocrine fashion.

Figure 1:
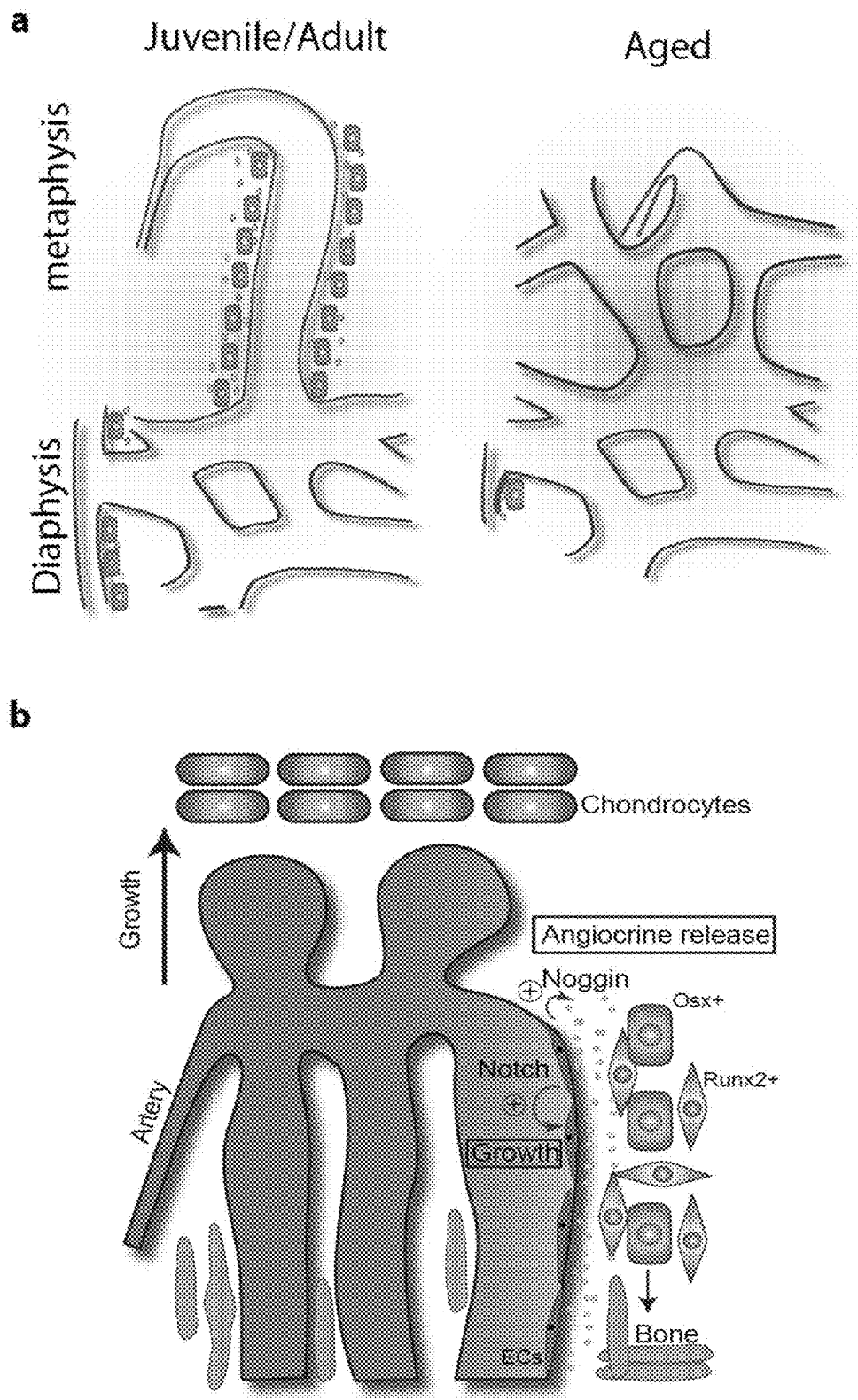
FIG. 1. a, Type H vasculature (red) in the metaphysis (mp) and endosteum (es) represents a functionally specialized vessel subtype that mediates vessel growth and promotes osteogenesis. The later is presumably mediated by angiocrine growth factors (small circles). In aged animals (right), the number of type H vessels and associated osteoprogenitors (OPs) is strongly reduced so that bone mainly contains type L, sinusoidal vessels characteristic for the diaphyseal (dp) marrow cavity.
Figure 2:
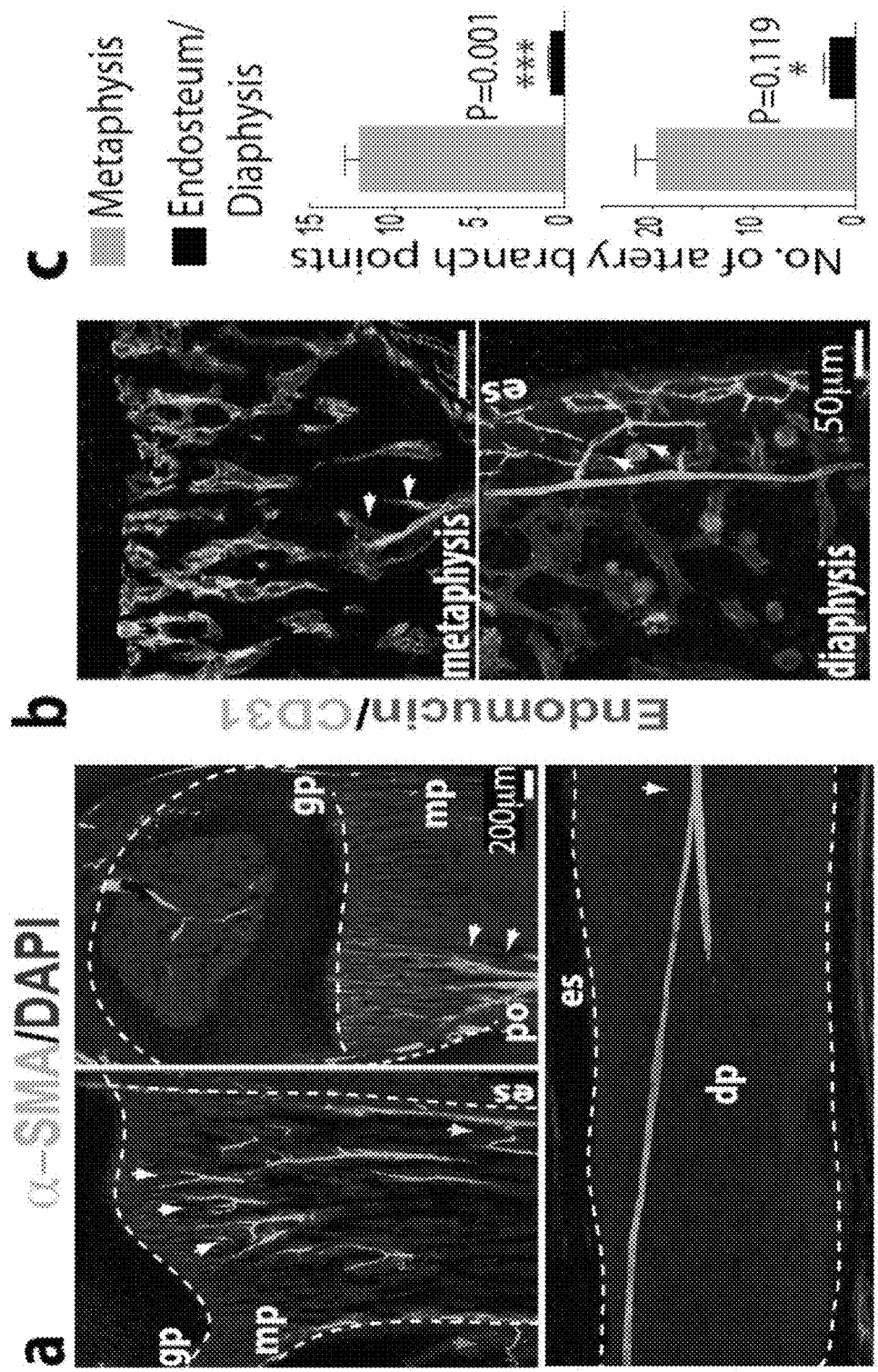

FIG. 2. a, α-SMA+ (white) arteries and α-SMA− CD31+ (green) Endomucin−(red) distal arterioles terminate in CD31+ Endomucin+capillaries within the metaphysis and endosteum (es, dotted line).

b, Quantitative analysis of branch points in α-SMA+ arteries within the metaphysis and diaphysis (endosteum) of 4 week-old tibia. Data represents mean±s.e.m (n=6).

c, Upper bar graph shows number of $CD31^{pos}$/endomucin$^{pos}$ artery branch points in metaphysis and diaphysis (endosteum) of long bone and lower bar graph shows number of $CD31^{pos}$/endomucin$^{neg}$ artery branch points. Error bars, ±s.e.m (n=4). P values, two-tailed unpaired t-tests.

Figure 3:
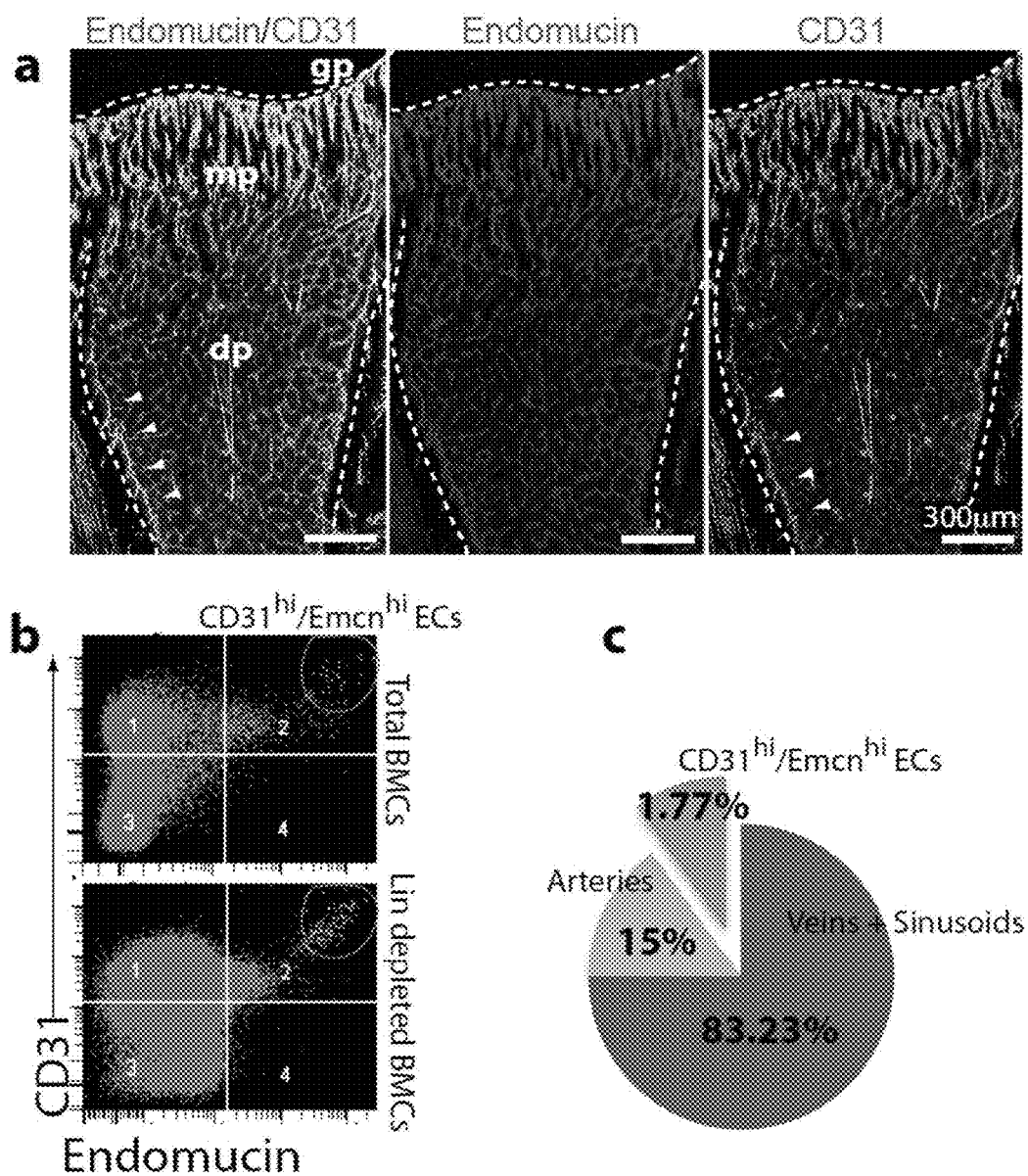

FIG. 3. a, Confocal tile scan of 4 week-old tibia images showing distinct patterns of CD31+ (green) and Endomucin+ (red) ECs. Nuclei, DAPI (blue). Strong CD31 and Endomucin signals mark capillaries in metaphysis (mp) and endosteum (arrowheads).

b, Representative flow cytometry dot plots showing the distinct $CD31^{hi}$ Endomucin$^{hi}$ EC subset in lineage (lin) depleted bone marrow cells.

c, Pie chart showing the relative abundance of EC subtypes in 4 week-old long bone. $CD31^{hi}/Emcn^{hi}$ cells represent 1.77±0.01% (mean±s.d.m of 7 mice) of total ECs.

Figure 4:
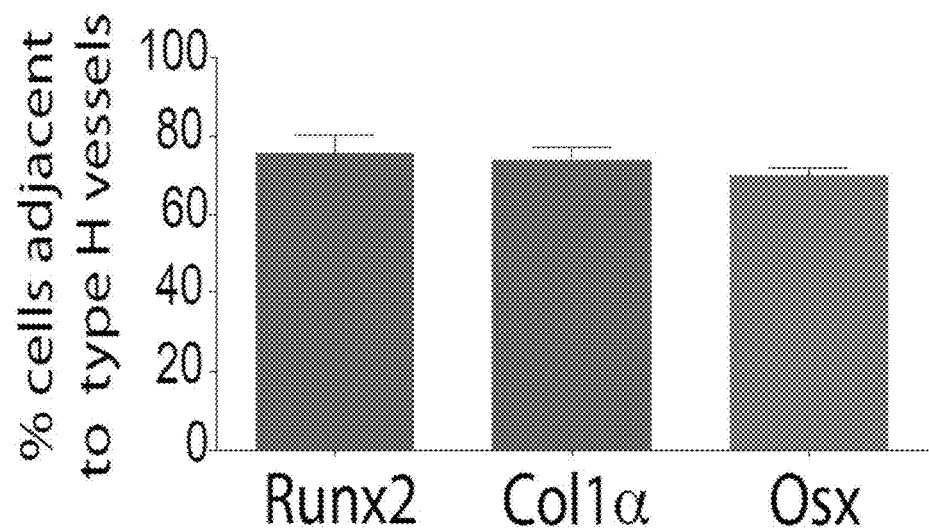

FIG. 4. Quantitative analysis of proximity (≤20 μm) of Runx2+, Collagen1α+ (Col1α) and Osterix+ (Osx) to nearest type H vessel. Mean±s.e.m, n=5.

Figure 5:
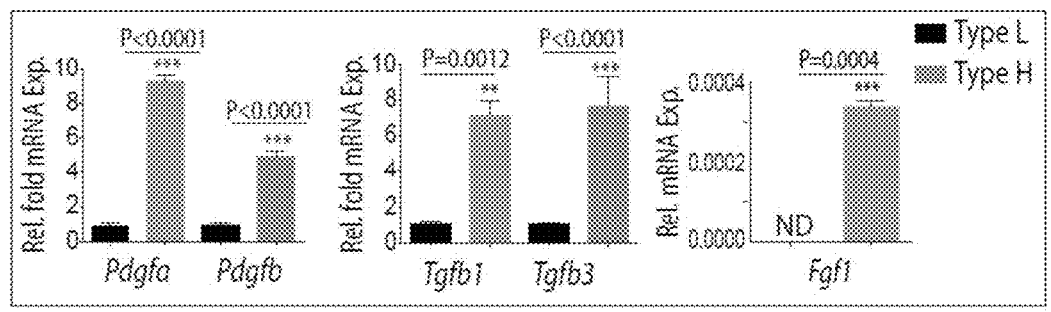

FIG. 5. a, qPCR analysis of growth factor expression (normalised to Actb) by $CD31^{hi}/Emcn^{hi}$ ECs relative to $CD31^{hi}/Emcn^{lo}$ ECs sorted from murine tibia. Data represent mean±s.e.m (n=4-6). P values, two-tailed unpaired t-test.

b, Representative confocal images of CD31 (green) and Endomucin (red) immunostained tibia sections at 4, 11 and 70 weeks. Note age-dependent decline of CD31+ Endomucin+ ECs in metaphysis (top row) and endosteum (es, arrowheads).

c, Quantitation of type H ($CD31^{hi}/Emcn^{hi}$) ECs from long bone of the indicated age group by flow cytometry. In bones adult mice (9-10 weeks of age) as compared to the juvenile mice (3-4 weeks of age) no significant change was observed for the total number of Ter119− CD45− CD31+ cells (bottom). Data represent mean±s.e.m (n=7).

d, Fold change in the number of EdU+ type H and type L ECs in murine tibia at the indicated ages determined by flow cytometry. Data represent mean±s.e.m (n=7).

Figure 6:
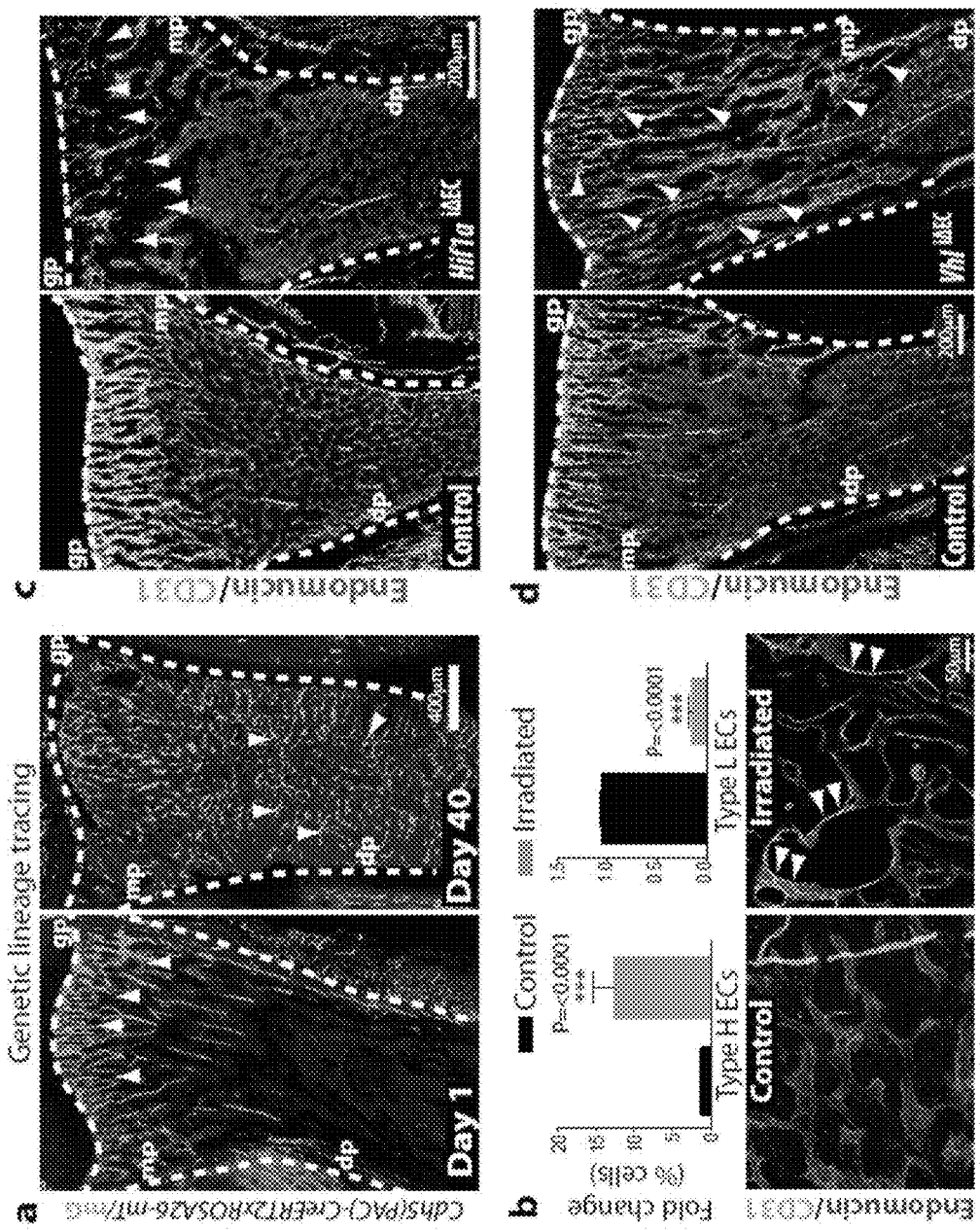

FIG. 6. a, Maximum intensity projection showing restricted GFP labelling (green) of arteries and $CD31^{hi}/Emcn^{hi}$ vessels in 4 week-old Cdh5(PAC)-CreERT2× ROSA26-mT/mG tibia at day 1 after administration of a single, low dose of tamoxifen (left). At day 40, GFP+ ECs were found throughout the metaphysis (mp) and diaphysis (dp, arrowheads). Nuclei, DAPI (blue).

b, Quantitative analysis of type H and type L ECs in long bone at 7 days after sublethal irradiation. Data represent mean±s.e.m (n=16). P values, two-tailed unpaired t-test.

Bottom panels show representative confocal images of control and irradiated diaphysis. CD31+ (green) Endomucin+ (red) ECs (arrowheads) were found throughout the diaphysis at 7 days after irradiation.

c, d, Maximum intensity projections of CD31 (green) and Endomucin (red) immunostained, 3 week-old $Hif1a^{i\Delta EC}$ (c) or $Vhl^{i\Delta EC}$ tibiae (d) with littermate controls. Note reduction of CD31+ Endomucin+ ECs (arrowheads) in $Hif1a^{i\Delta EC}$ metaphysis (mp), but their expansion in $Vhl^{i\Delta EC}$ samples. Growth plate, gp; Diaphysis, dp.

Figure 7:
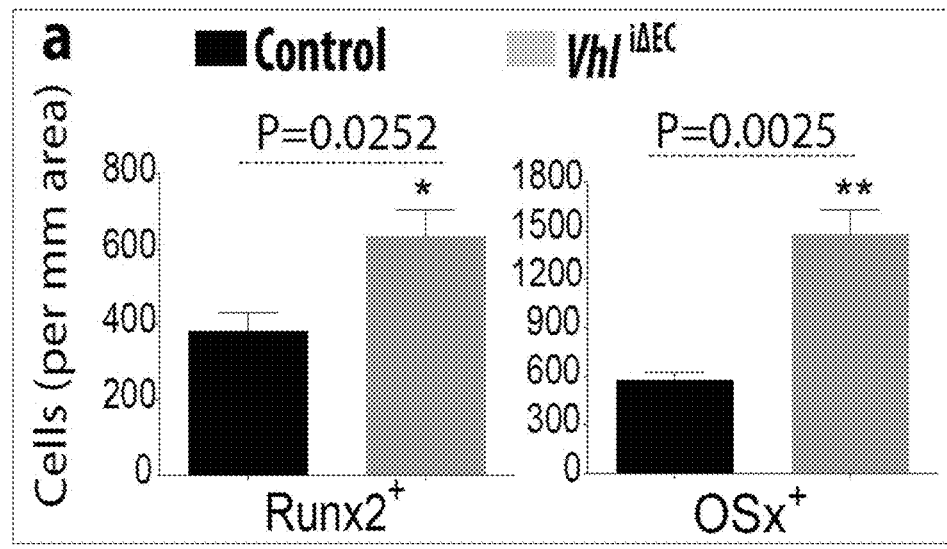

FIG. 7. a, Quantitation of Runx2+ and Osterix+ in $Vhl^{i\Delta EC}$ mutants and littermate controls. Data represent mean±s.e.m (n=5). P values, two-tailed unpaired t-test.

Figure 8:
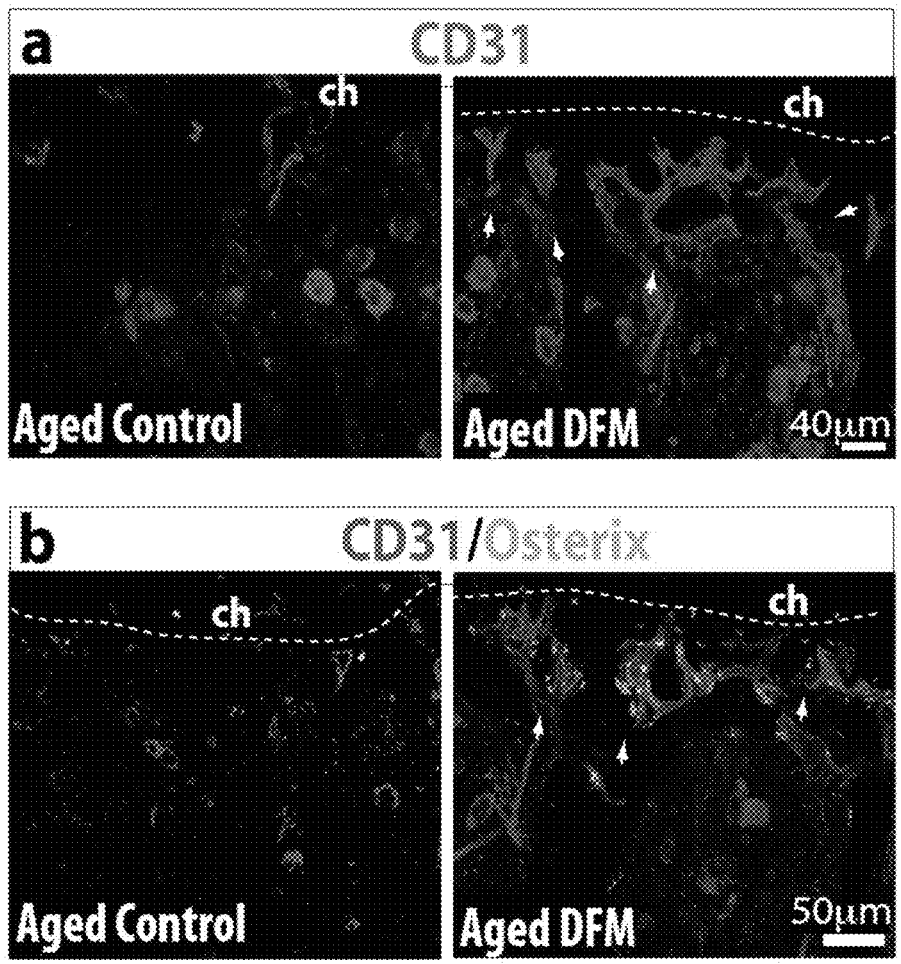

FIG. 8. a, b, Representative confocal images of CD31 (red, f) or CD31 and Osterix (green, g) stained tibia sections from aged DFM-treated and control mice. Low intensity projection shows only $CD31^{hi}$ cells. DFM induces $CD31^{hi}$ vessels and Osterix+ osteoprogenitors. Chondrocytes, ch.

Figure 9:
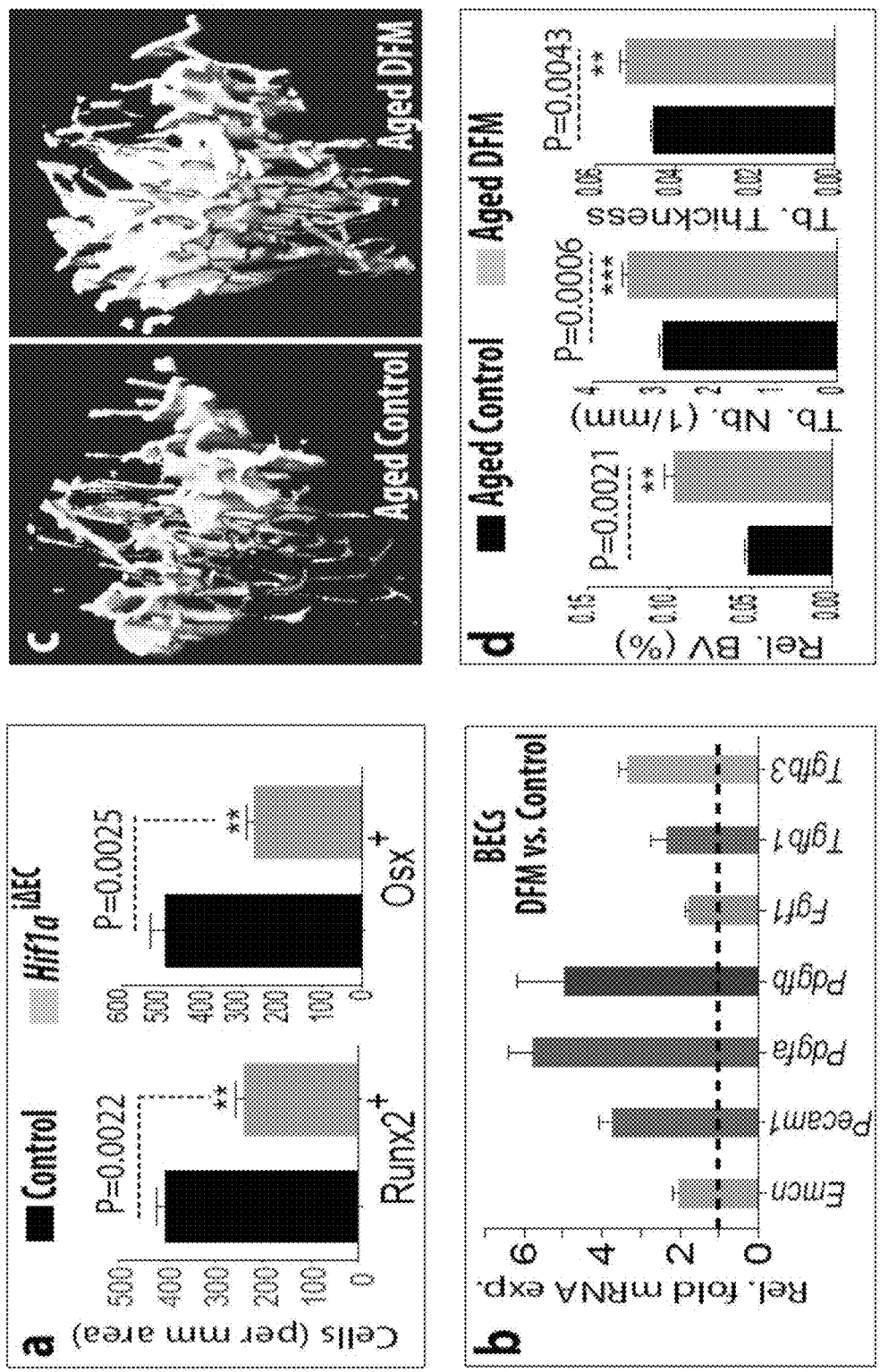

FIG. 9. a, Quantitation of Runx2+ and Osterix+ in $Hif1a^{i\Delta EC}$ mutant and control long bone. Data represent mean±s.e.m (n=5). P values, two-tailed unpaired t-test.

b, qPCR mRNA analysis of DFM or vehicle-treated bone endothelial cells (BECs). Data represent mean±s.e.m (n=3). Note induction of growth factor expression by DFM c, Representative μ-CT images of tibias from aged DFM-treated and control mice.

d, Quantitative μ-CT analysis of relative bone volume (Rel. BV), trabecular number (Tb. Nb), and trabecular thickness (Tb. Thickness) in proximal tibia from aged DFM-treated and control mice. Data represent mean±s.e.m (n=5). P values, two-tailed unpaired t-test.

Figure 10:
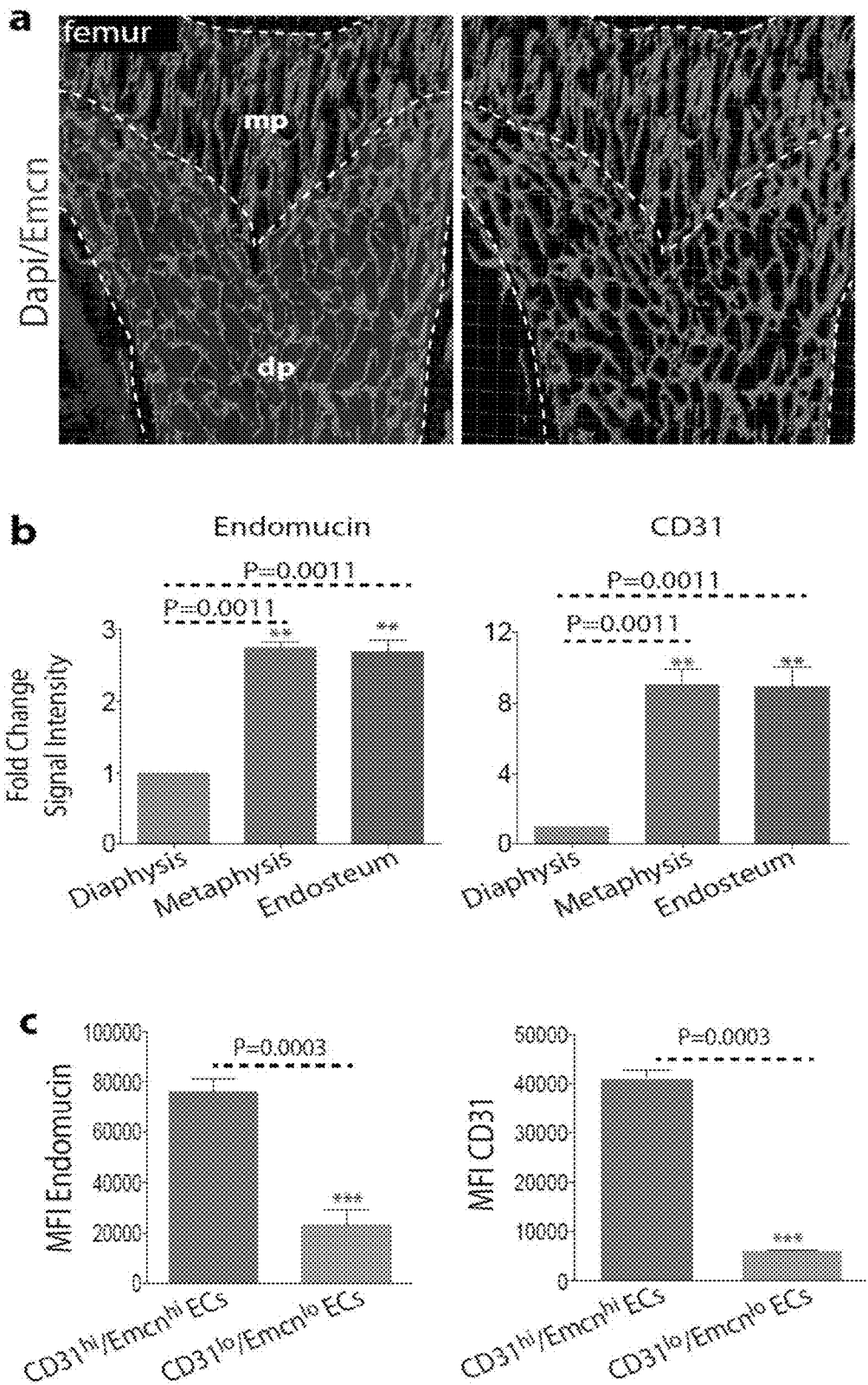

FIG. 10. a, Representative tile scan confocal image showing Endomucin (Emcn, red) immunostaining of ECs in the femur of a juvenile mouse. Nuclei in left image are stained with DAPI (blue). Dotted lines indicate the adjacent growth plate (top) or the border of the diaphysis (dp). Note distinct morphologies of metaphyseal (mp) and diaphyseal vessels.

b, Quantitative analysis of relative CD31 and Endomucin immunostaining intensities in the microvasculature of the metaphysis, diaphysis (marrow cavity) and endosteum. Data represent mean±s.e.m (n=7). P values, two-tailed unpaired t-test.

c, Mean fluorescence intensities (MFI) of $CD31^{hi}$/endomucin$^{hi}$ and $CD31^{lo}$/endomucin$^{lo}$ endothelial subsets as determined by flow cytometric analysis of bone marrow cells stained with CD31 and endomucin. Data represent mean±s.e.m (n=7). P values, two-tailed unpaired t-test.

Figure 11:
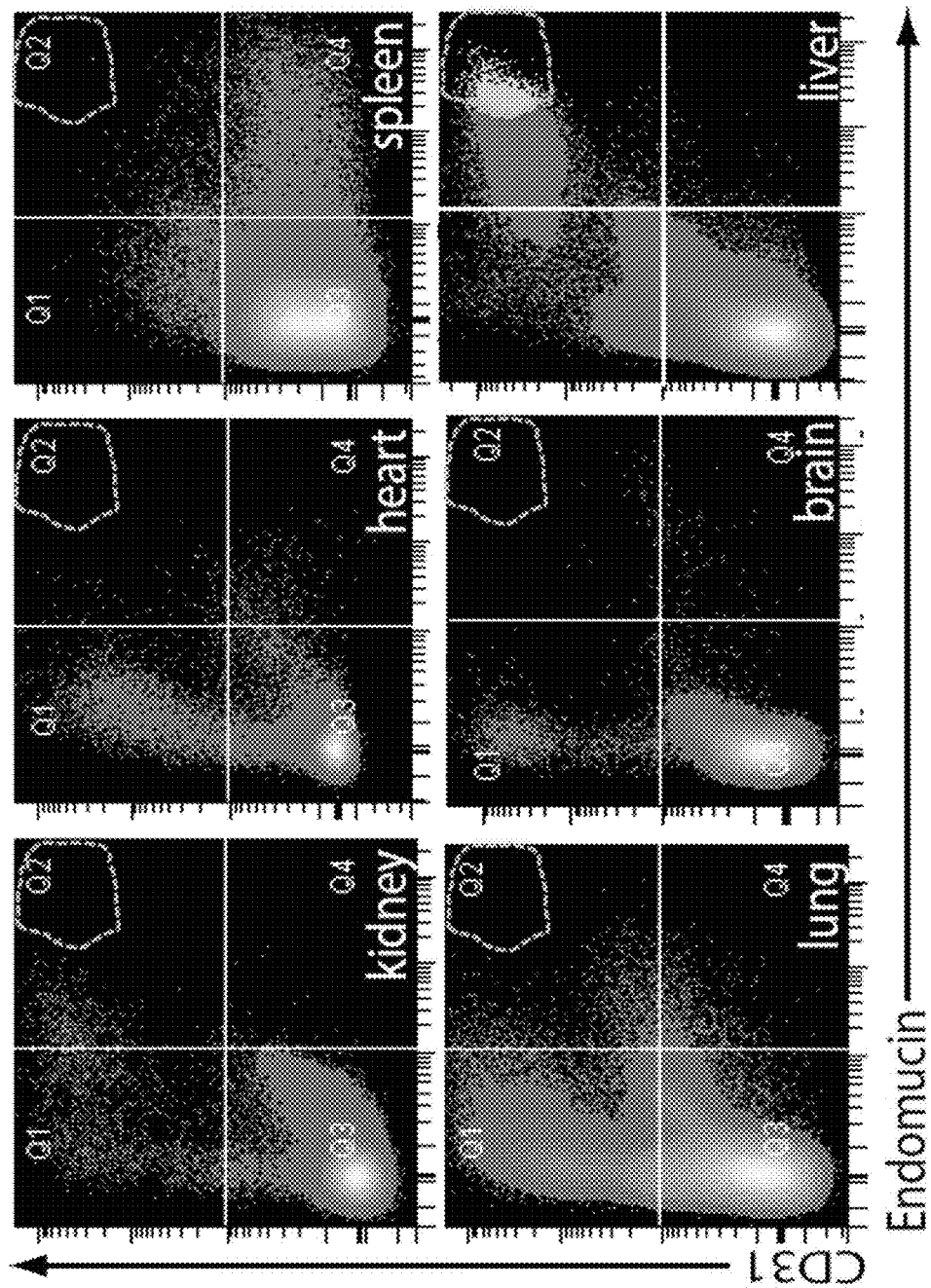

FIG. 11. Representative dot plots showing flow cytometric analysis of CD31 and Endomucin stained single cell suspensions from kidney, heart, spleen, lung, brain, and liver. Note absence of a $CD31^{hi}/Emcn^{hi}$ EC subset (orange dotted circle in Q2) in these organs with exception of liver.

Figure 12:
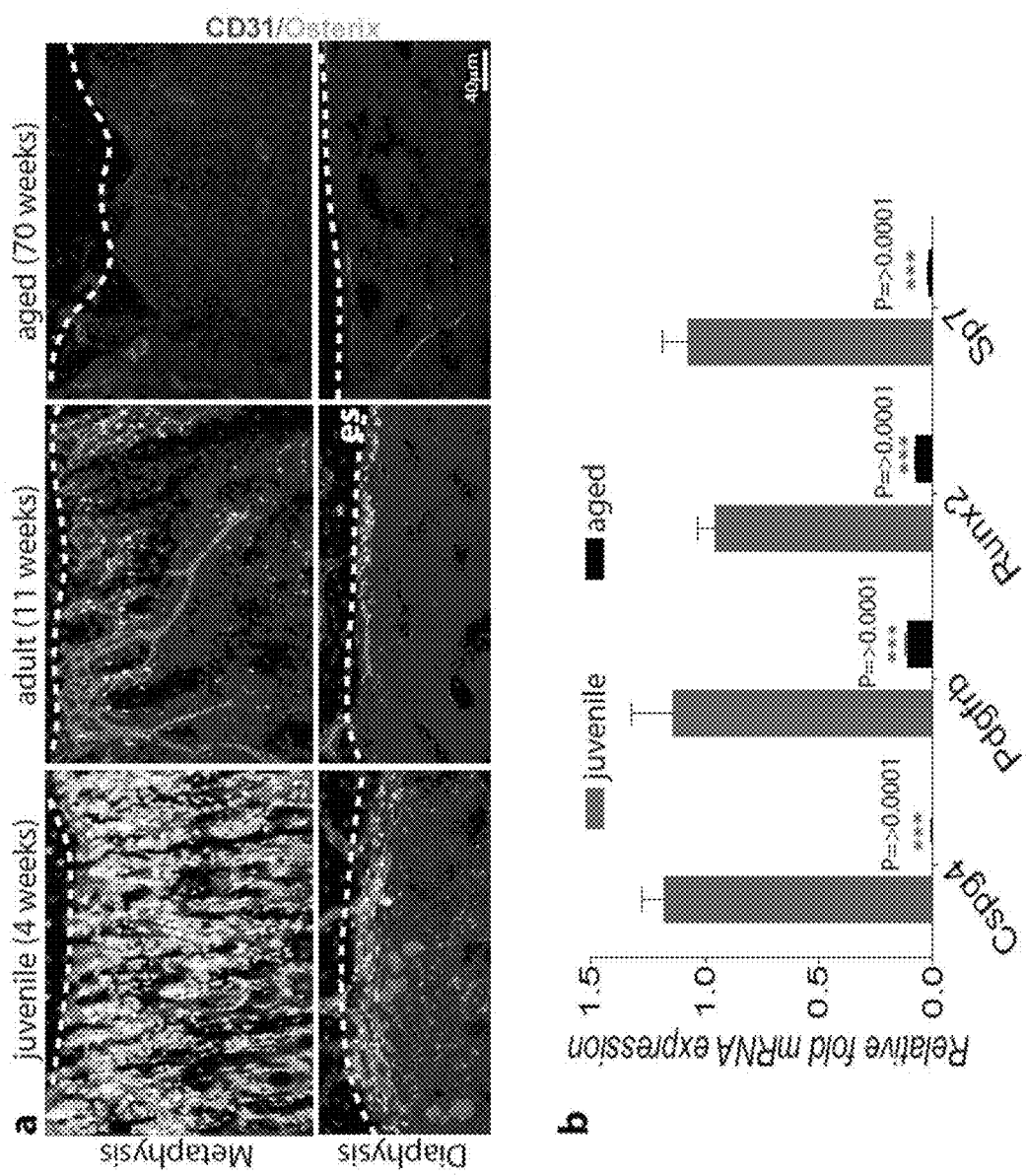

FIG. 12. a, Representative confocal images from metaphyseal and diaphyseal regions of tibias from mice of different ages immunostained for Osterix (green) and CD31 (red). Nuclei, DAPI (blue). Dotted lines mark the adjacent growth plate (metaphysis) or endosteum (es) in diaphysis. Note striking decline of CD31+ vessels and associated osteoprogenitors in aging mice.

b, Quantitative mRNA expression analysis of Cspg4, Pdgfrb, Runx2, and SP7 relative to transcripts encoding p-actin in long bones from juvenile and aged mice. Note significant decline of all 4 markers in bone from aged mice. Data represent mean±s.e.m (n=7). P values, two-tailed unpaired t-test.

Figure 13:
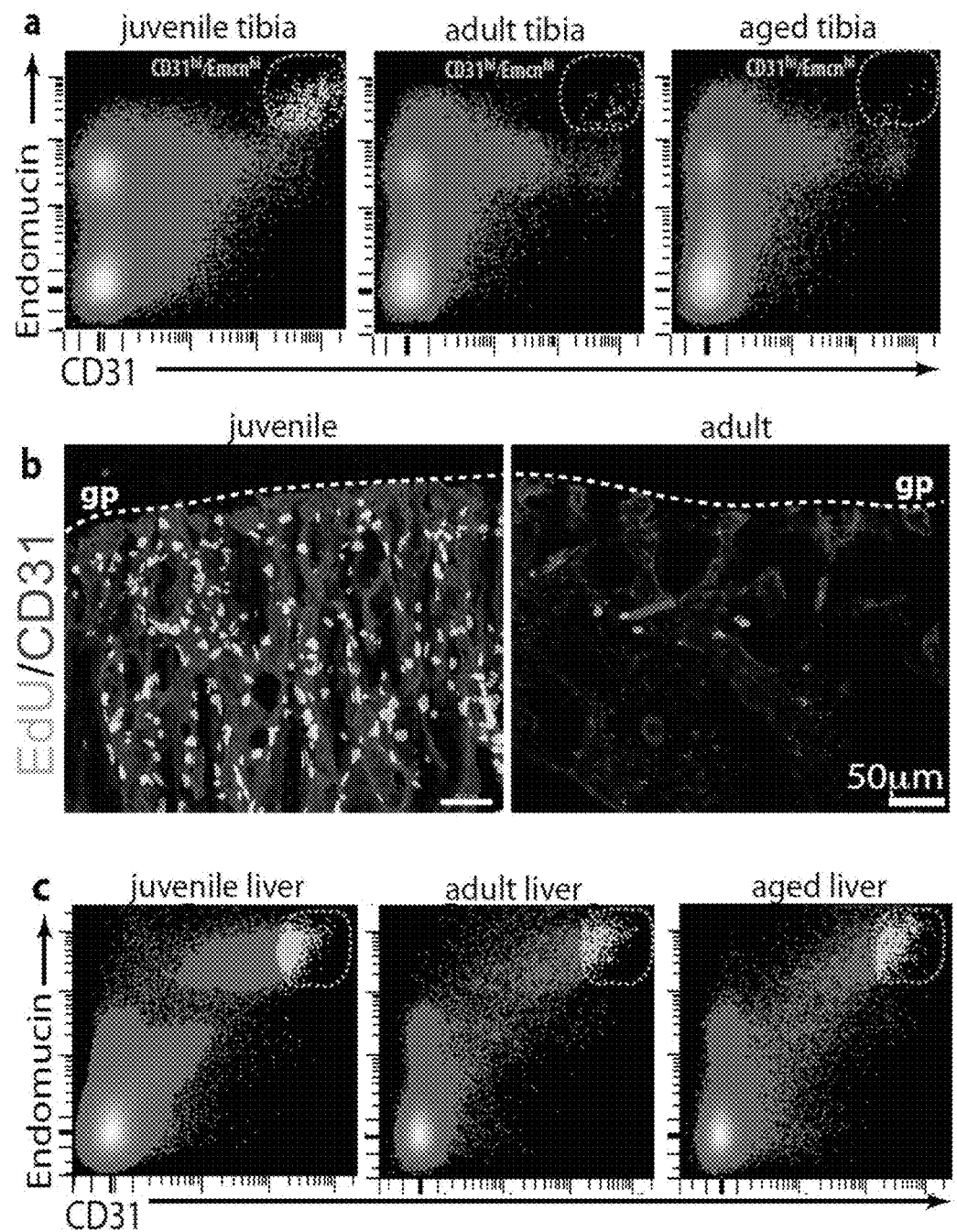

FIG. 13 a, FACS plots of CD31 and Endomucin double stained single cell suspensions from murine tibias. $CD31^{hi}/Emcn^{hi}$ ECs decline with age.

b, Representative confocal images showing CD31 immunostaining (red) and proliferation (EdU incorporation, green) in tibial metaphysis near the growth plate (gp). The number of proliferating cells and CD31+ vessels is strongly reduced in adult mice relative to juvenile animals.

c, FACS plots showing CD31 and endomucin double staining of single cell suspensions from juvenile, adult and aged mice livers. $CD31^{hi}/Emcn^{hi}$ ECs in liver do not decline with age.

Figure 14:
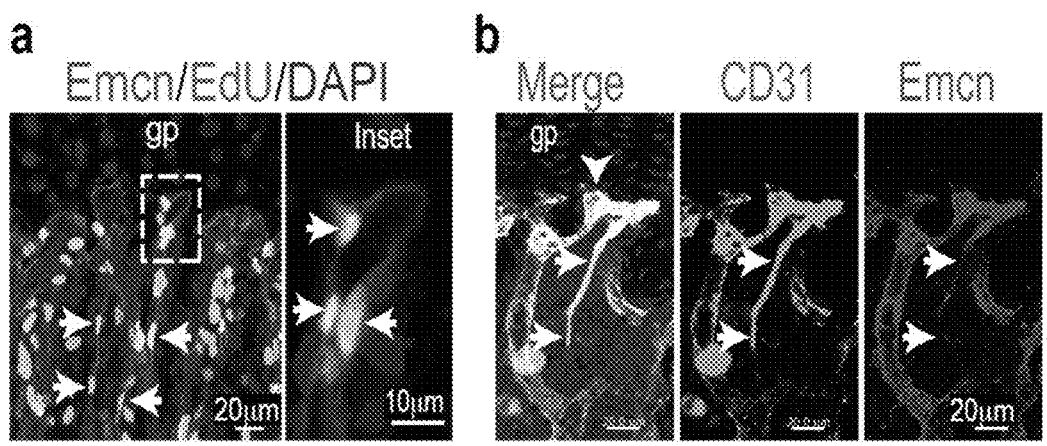

FIG. 14. a, Maximum intensity projection showing proliferating (EdU-labelled) cells (bright dots) in the metaphysis. ECs, endomucin (Emcn, grey); nuclei, DAPI (round, dark grey). Note abundance of EdU+ ECs in column structures. Inset shows single plane of EdU+ ECs in vessel arch. b, Vascular front from tibia of a 10 week old mice showing an CD31+ (light grey) Emcn– (dark grey) arteriole (arrows) connecting to a CD31+ Emcn+ vascular arch (arrowhead). Brighter vessels in merged image. Nuclei, DAPI (Dark grey dots).

Figure 15:
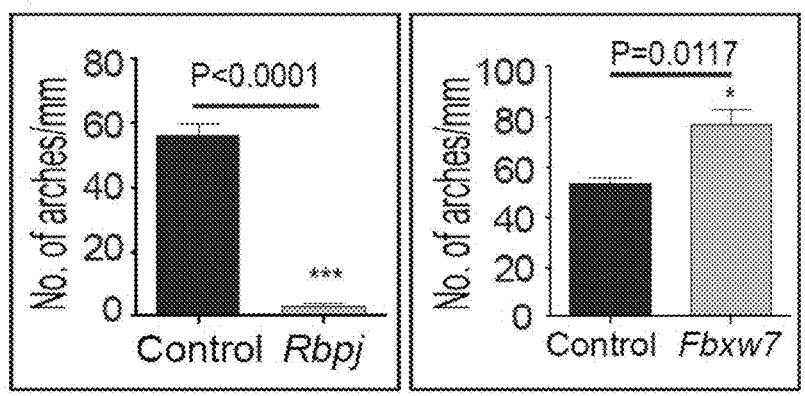
Figure 15:
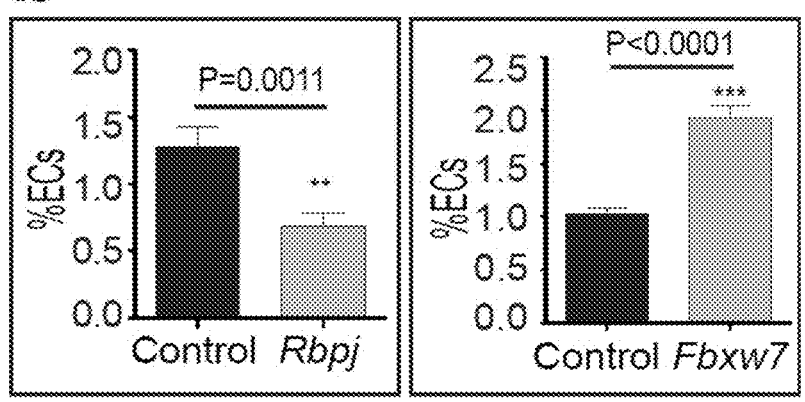
Figure 15:
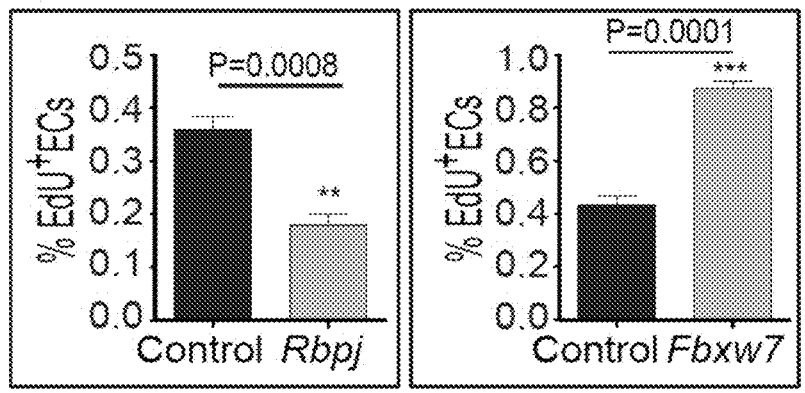

FIG. 15. a, Number of distal arches (per mm length of metaphysis) was reduced in $Rbpj^{i\Delta EC}$ tibiae and increased in $Fbxw7^{i\Delta EC}$ samples. Error bars, ±s.e.m. P values, two-tailed unpaired t-tests.

b, c, Flow cytometric quantitation of percentage of total (CD45− Ter119− CD31+) ECs (b) and EdU+ ECs (c) in $Rbpj^{i\Delta EC}$ or $Fbxw7^{i\Delta EC}$ bone samples relative to littermate controls. Error bars, ±s.e.m. P values, two-tailed unpaired t-tests.

Figure 16:
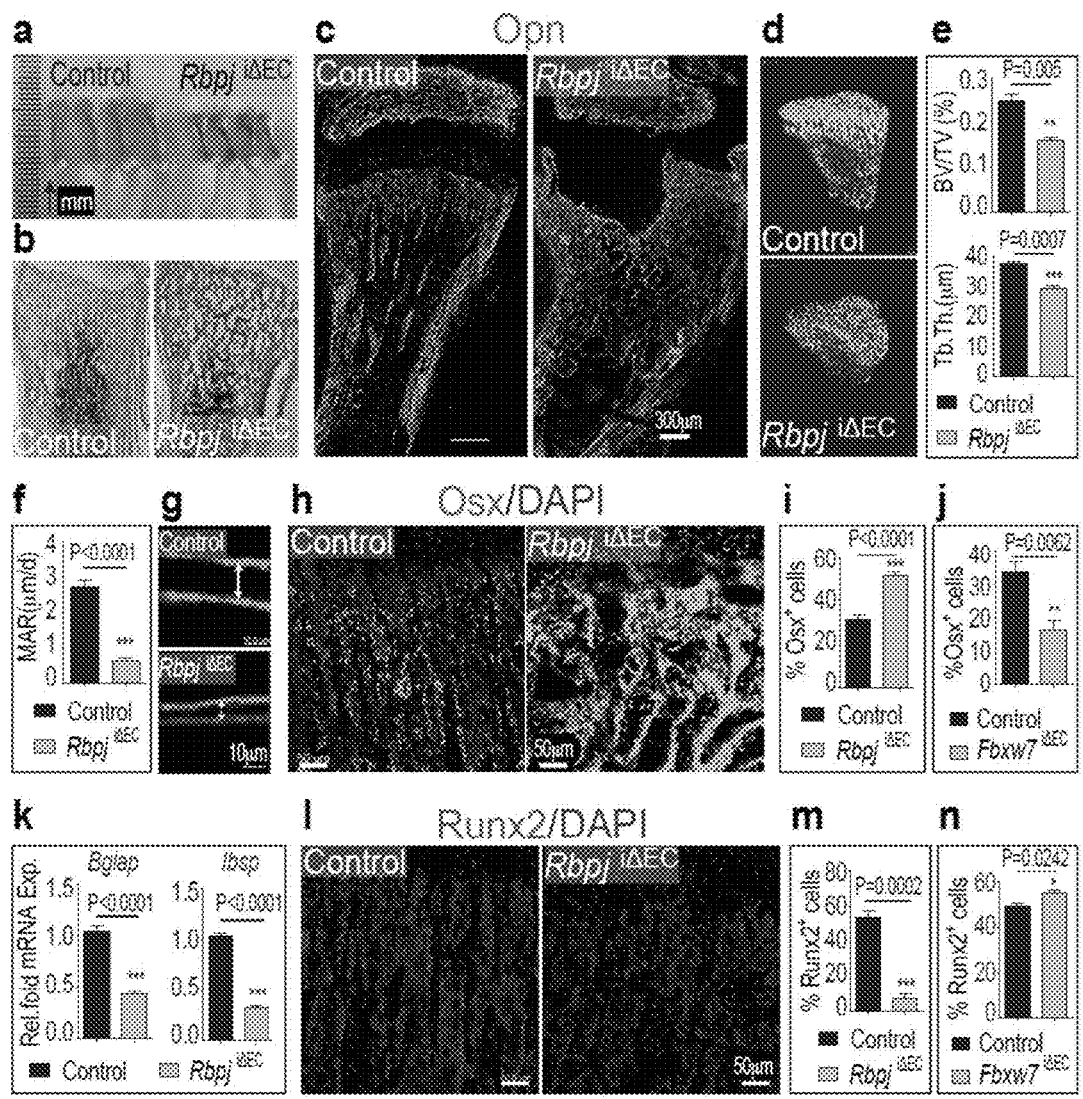

FIG. 16. a, Deceased length of freshly dissected $Rbpj^{i\Delta EC}$ femurs compared to control littermates.

b, Hematoxylin and eosin stained longitudinal $Rbpj^{i\Delta EC}$ and control tibia sections.

c, Osteopontin (Opn) immunostaining showing defective formation of trabeculae in $Rbpj^{i\Delta EC}$ tibia.

d, 3D reconstruction of 4 week-old control and $Rbpj^{i\Delta EC}$ metaphysis by μ-CT.

e, Reduced trabecular bone volume density measured as bone volume/total volume (BV/TV) and trabecular bone thickness (Tb.Th) in $Rbpj^{i\Delta EC}$ mice.

f, g, Mineral apposition rates (MAR, f) calculated by calcein double labelling (7 day time interval, g) confirmed decreased bone formation in P28 Rbpj mutants. Arrows in (g) mark distance between calcein-labelled layers. Error bars, ±s.e.m. P value, two-tailed unpaired t-tests.

h, Immunostaining of Osterix (Osx) and shows strongly increased number of osteoprogenitor cells in $Rbpj^{i\Delta EC}$ metaphysis. Nuclei, DAPI (light grey).

j, Quantitation of metaphyseal Osx+ cells in $Rbpj^{i\Delta EC}$ (i) and $Fbxw7^{i\Delta EC}$ mutants (j) relative to littermate controls. Error bars, ±s.e.m. P values, two-tailed unpaired t-tests.

k, qPCR analysis showing reduced expression of mature osteoblast markers (Bglap, lbsp) in $Rbpj^{i\Delta EC}$ bones.

l, Immunostaining showing decrease of Runx2+ early osteoprogenitors in 4 week-old in $Rbpj^{i\Delta EC}$ tibiae. Nuclei, DAPI (light grey).

m, n, Quantitation of metaphyseal Runx2+ cells in Rbpj (m) and $Fbxw7^{i\Delta EC}$ mutants (n) relative to littermate controls. Error bars, ±s.e.m. P values, two-tailed unpaired t-tests.

Figure 17:
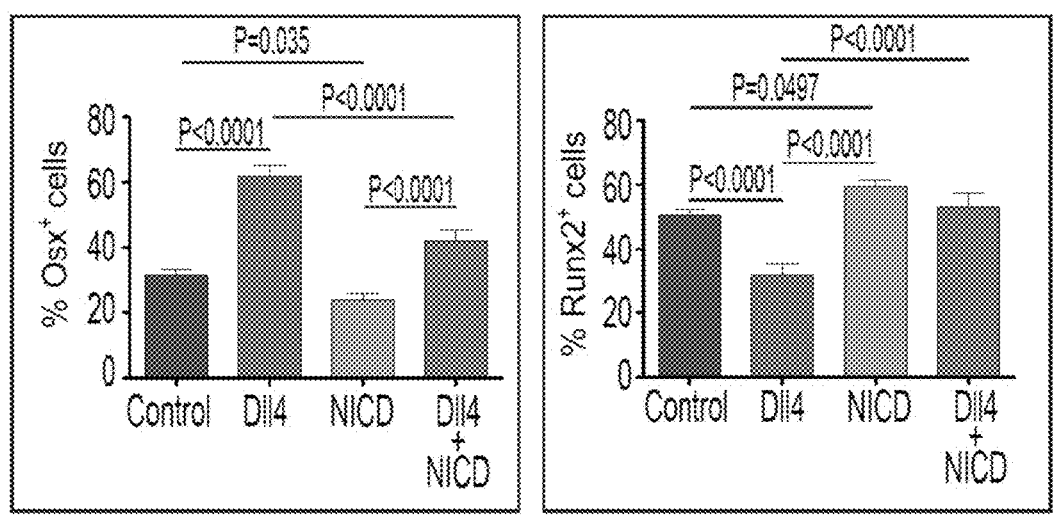

FIG. 17. Quantitative analysis of Osx+ and Runx2+ cell populations in (Cre-negative) control, $Dll4^{i\Delta EC}$ (Dll4) or $NICD^{iOE-EC}$ (NICD) single mutant, or $Dll4^{i\Delta EC}$, $NICD^{iOE-EC}$ (Dll4+NICD) double mutant tibiae, as indicated. Control in all the panels represents the littermate animals without Cre expression. Error bars, ±s.e.m. P values, one-way ANOVA with Bonferroni's multiple comparison post-hoc test.

Figure 18:
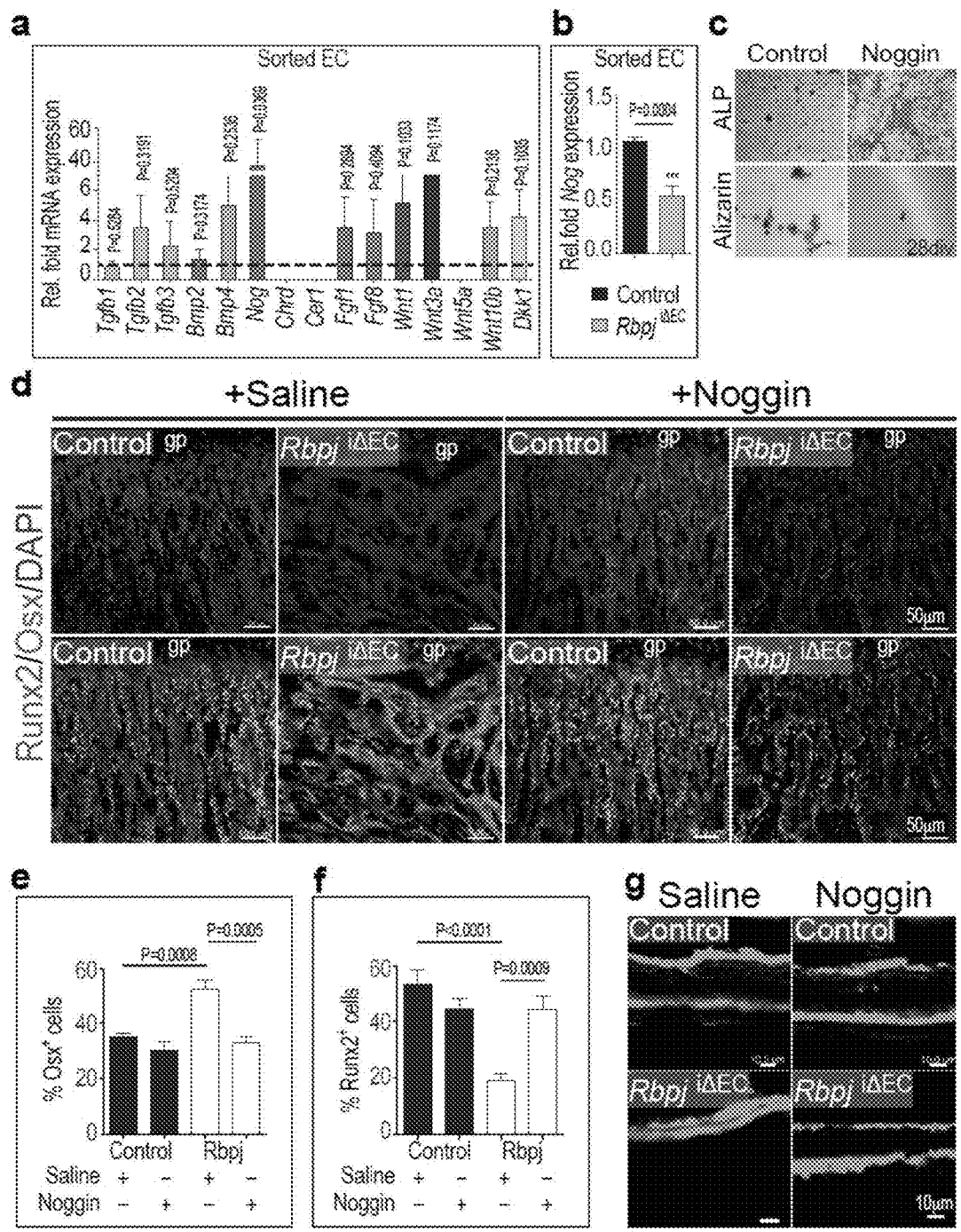

FIG. 18. a, Tgfb2, Bmp4, Fgf1, Fgf8, Nog, Wnt1, Wnt3a, Wnt10b, and Dkk1 mRNA expression in isolated bone ECs from $Fbxw7^{i\Delta EC}$ mice normalized to expression in littermate controls (dotted line). 40-fold increased expression of Noggin (Nog). Error bars, ±s.e.m.

b, qPCR analysis showing reduced Nog expression in ECs sorted from $Rbpj^{i\Delta EC}$ long bone mice expressed decreased Noggin transcripts level. Error bars, ±s.e.m. P value, two-tailed unpaired t-test.

c, Inhibition of osteoblastic differentiation of cultured murine mesenchymal progenitors by Noggin administration. Mineral nodule formation (Alizarin staining) was supressed, and alkaline phosphatase (ALP) enhanced in Noggin-treated samples after 28 days of in vitro differentiation.

d, Systemic administration of recombinant Noggin protein reduced the number of Osx+ cells and increased Runx2+ early osteoprogenitors in the $Rbpj^{i\Delta EC}$ metaphysis in comparison to vehicle-treated (Saline) mutants. Nuclei, DAPI.

e, f, Quantitation of Osx+ (e) and Runx2+ cells (f) in Noggin-treated vs. Saline-injected control and $Rbpj^{i\Delta EC}$ long bones. Error bars, ±s.e.m. P values, one-way ANOVA with Bonferroni's multiple comparison post-hoc test.

g, Calcein double labelling in $Rbpj^{i\Delta EC}$ mutant or (Cre-negative) littermate control tibiae treated with Saline or Noggin, as indicated. Note that Noggin restored mineral apposition rate in $Rbpj^{i\Delta EC}$ animals.

Figure 19:
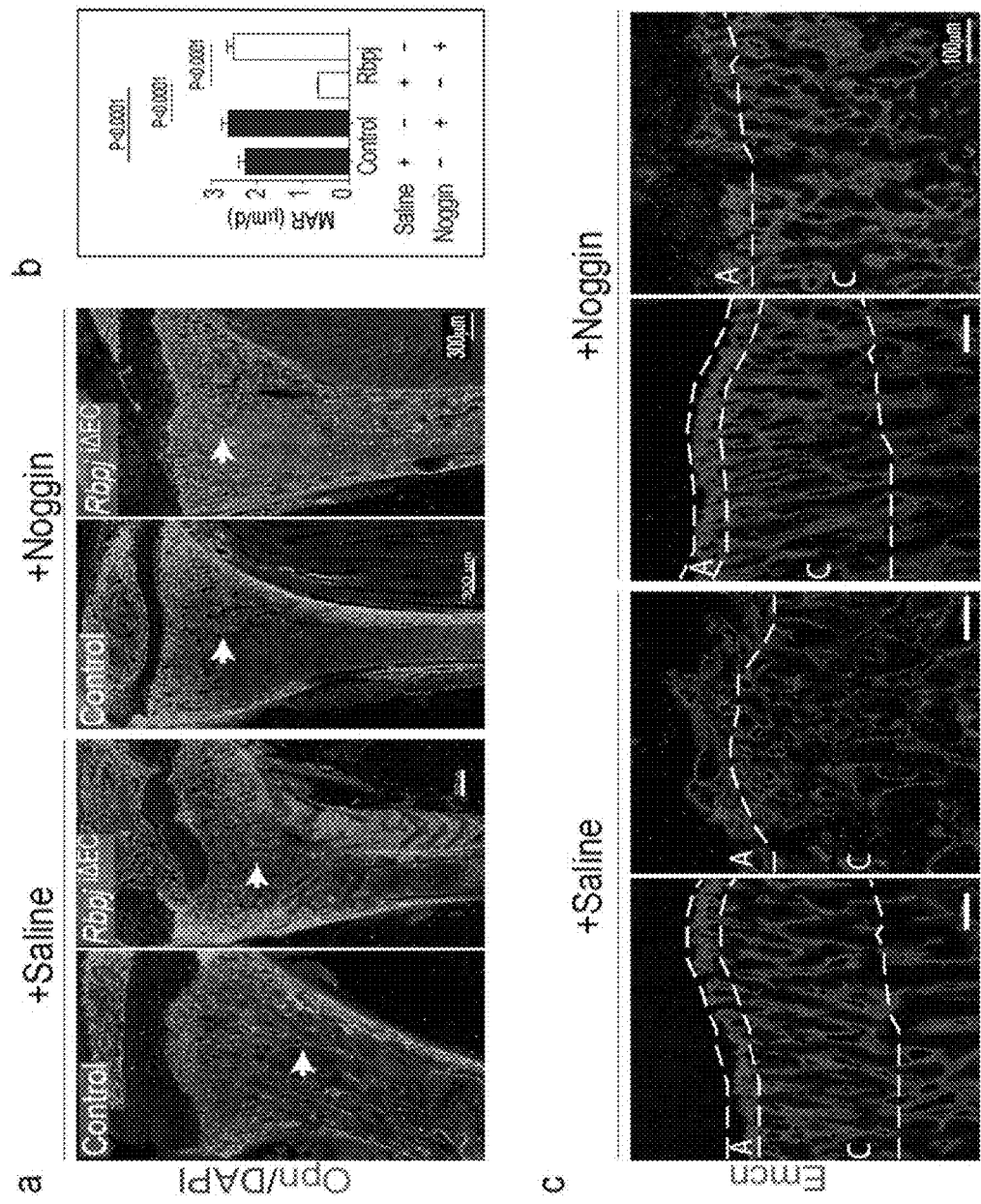

FIG. 19. Notch and angiocrine Noggin production.

a, Confocal tile scans of osteopontin-immunostained tibia sections showing partial restoration of trabecular bone formation in $Rbpj^{i\Delta EC}$ mice by administration of recombinant Noggin. Left panels show Saline-treated $Rbpj^{i\Delta EC}$ mutants and littermate controls. Nuclei, DAPI.

b, Noggin treatment restored the mineral apposition rate in $Rbpj^{i\Delta EC}$ long bone to control level. Data represent mean±s.e.m. One-way ANOVA was performed along with Bonferroni's multiple comparison post-hoc test.

c, Maximum intensity projection of endomucin-immunostained (Emcn, grey) of control and Rbpj$^{i\Delta EC}$ tibia sections after treatment with Saline or recombinant Noggin, as indicated. Endomucin staining intensity was increased in Noggin-treated Rbpj$^{i\Delta EC}$ samples, and the organisation of endothelial column and arch structures was partially restored. Dotted lines indicate position of column-arch boundaries as seen in littermate control samples.

Figure 20:
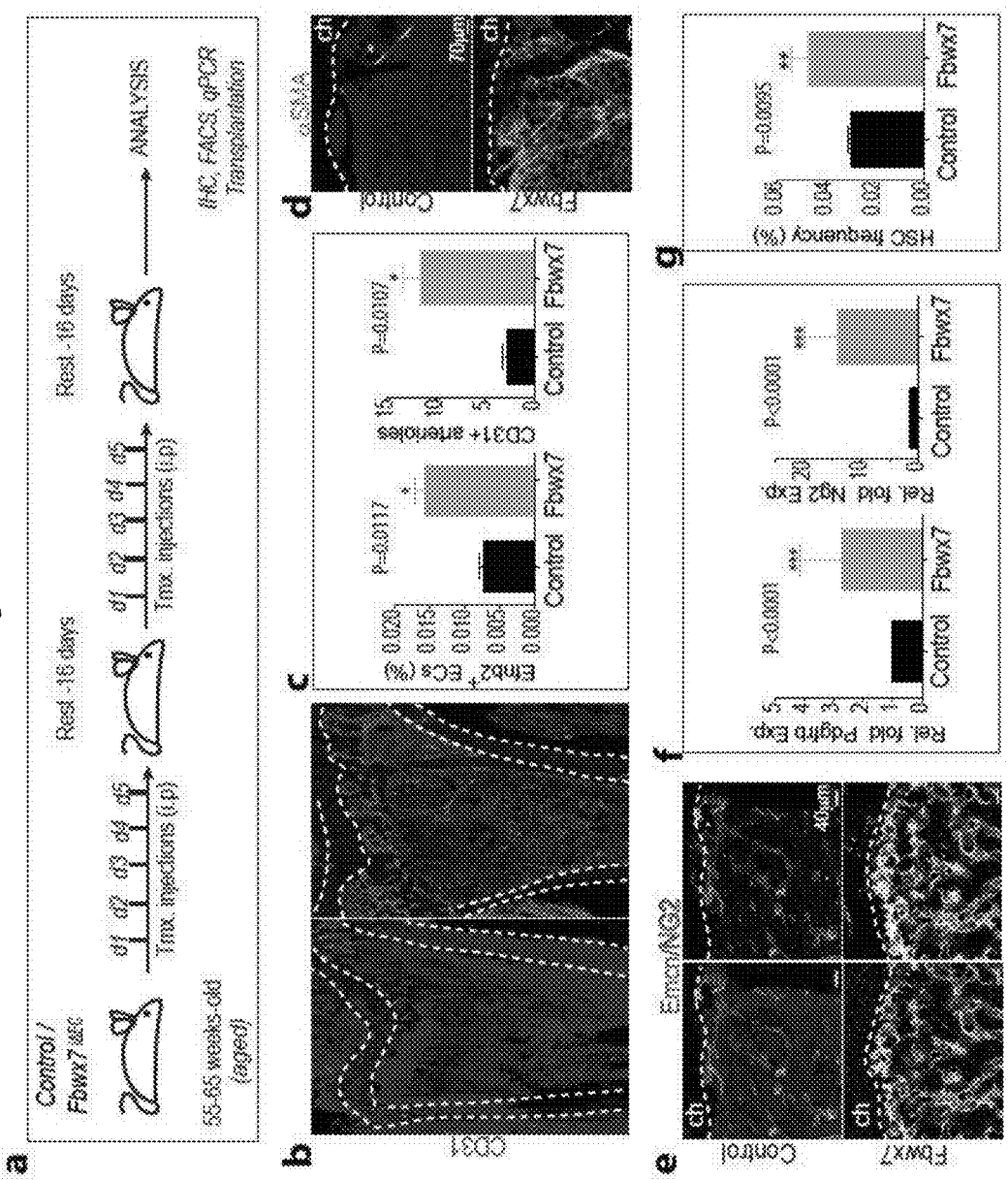

FIG. 20. Endothelial cell-specific inhibition of Fbxw7 reactivates type H endothelial cells in bone of aged mice and thereby improves stromal and hematopoietic stem cells.

a, Schematic illustrating the tamoxifen injection and analysis strategy for the aged Fbxw7i$\Delta$EC mutants and their littermate controls.

b, Representative tile scan confocal images showing CD31 (light grey) expressing blood vessels in aged Fbxw7i$\Delta$EC mutants and littermate control tibia. Note the increase in CD31 positive capillaries in the section from Fbxw7iEEC mutant tibia as compared to littermate control tibia.

c, Quantitation of Efnb2+ ECs (left panel) from long bones of Fbxw7i$\Delta$EC mutants and littermate controls by flow cytometry. Data represents mean±s.e.m (n=5). P values, two-tailed unpaired t-test. Bar graph in the right panel shows quantitative analysis of CD31+ arterioles within the metaphysis region of Fbxw7i$\Delta$EC mutant and littermate control mice tibias. Data represents mean±s.e.m (n=4). P values, two-tailed unpaired t-test. Note the increase in Efnb2+ ECs and CD31+ arterioles in Fbxw7i$\Delta$EC mutant bones.

d, Representative confocal images of the tibial sections from Fbxw7i$\Delta$EC mutant and littermate control tibias as indicated showing α-SMA+ immunostaining in the metaphysis region. Dashed lines mark the chondrocyte (ch) zone.

e, Representative confocal images of the tibial sections from Fbxw7i$\Delta$EC mutant and littermate control tibia showing Ng2+ (white) cells in the metaphysis region of bone. Emcn immunostaing (grey) marks the blood vessels. Dashed lines mark the chondrocyte zone (ch). Note the remarkable increase in Ng2 signal in the Fbxw7i$\Delta$EC mutant tibia.

f, qPCR analysis of Pdgfrb and Ng2 expression (normalised to Actb) in the long bones of Fbxwi$\Delta$EC mutants compared to littermate controls. Data represents mean±s.d (n=4). P values, two-tailed unpaired t-test. Note the increase in Pdgfrb and Ng2 expression in the long bone of Fbxwi$\Delta$EC mutants as compared to littermate controls.

g, Quantitation of HSCs in the long bones of Fbxwi$\Delta$EC mutants relative to littermate controls. Data represents mean±s.e.m (n=5–6). P values, two-tailed unpaired t-test. Note the significant increase in HSC frequency in Fbxwi$\Delta$EC mutant bones.

Figure 21:
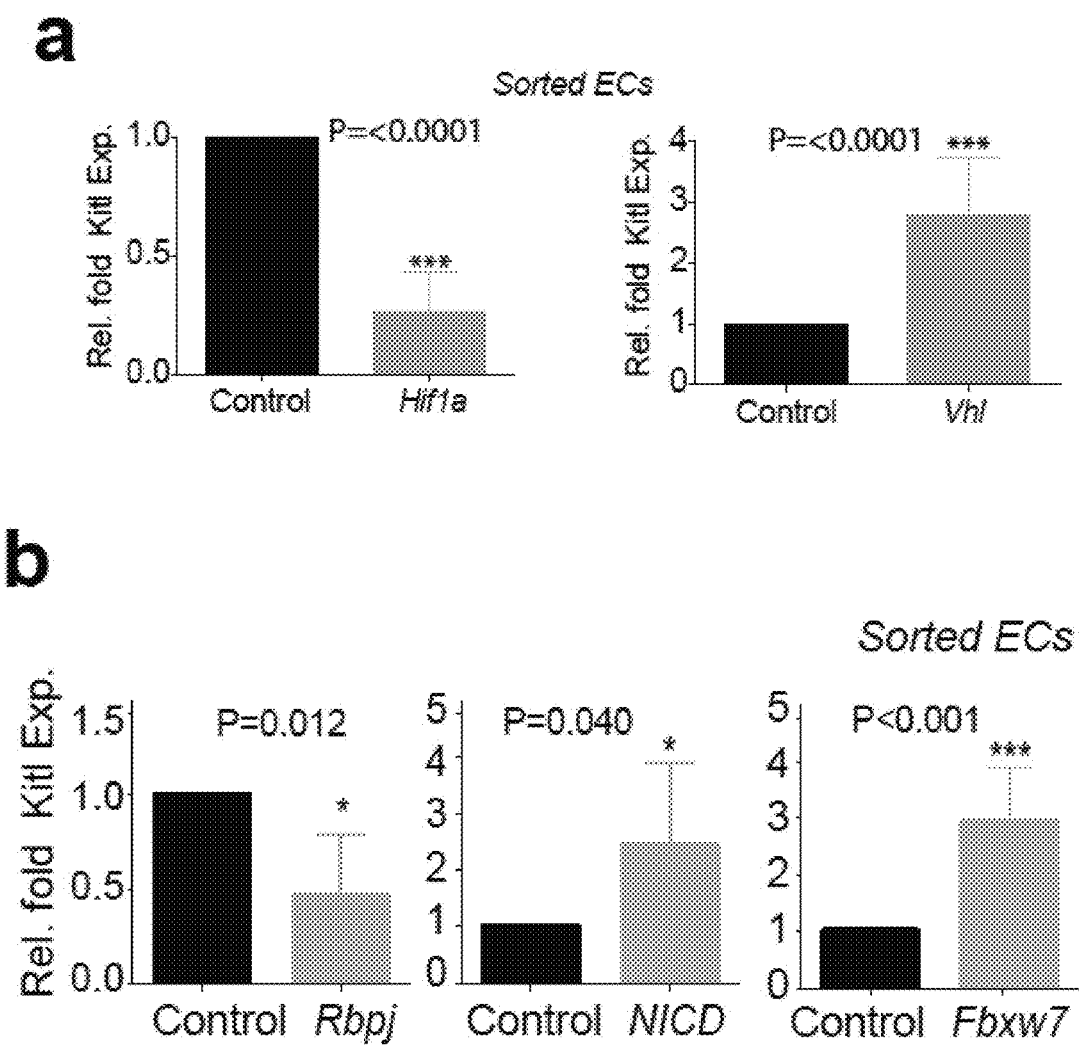

FIG. 21. qPCR analysis Kitl a,b, qPCR analysis showing the positive regulation of stem cell factor expression (Kitt gene) in ECs sorted from Vhl$^{i\Delta EC}$ long bone (a), from Fbxw7$^{i\Delta EC}$ mutants or from mice overexpressing active Notch1 intracellular domain (NICD) in endothelial cells (b). Conversely, Kitl expression was reduced in ECs isolated from Hifl$^{i\Delta EC}$ (a) or Rbpj$^{i\Delta EC}$ (b) mutant long bones. Error bars, ±s.e.m. P value, two-tailed unpaired t-test.

FIG. 22. provides Table 2 that shows the results of a comparison of gene expression in type H bone endothelial cells and type L bone endothelial cells.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Methods

Genetically Modified and Aged Mice 3-4 weeks old male C57BL/6J mice were used for experiments involving analysis of juvenile mice. For the characterization of changes during aging, 9-11 week-old and 60-70 week-old C57BL/6J males were used as adults and aged mice, respectively. All EC-specific gene deletions were generated using Cdh5(PAC)-CreERT2 transgenic mice, which were interbred with conditional mutants carrying loxP-flanked Hifl$\alpha$ alleles (Hifl$\alpha^{lox/lox}$). For experiments, Cdh5(PAC)-CreERT2$^{T/+}$ Hifl$\alpha^{lox/lox}$ were mated with Hifl$\alpha^{lox/lox}$ females. To induce Cre activity and gene deletion, pups were injected with 500 μg tamoxifen (Sigma, T5648) intraperitoneally everyday from postnatal day (P) 10 to P14. Femurs and tibiae from Cdh5(PAC)-CreERT2$^{T/+}$ Hifl$\alpha^{lox/lox}$ (Hifl$\alpha^{i\Delta EC}$) mutants and Cre-negative (Hifl$\alpha^{lox/lox}$) controls were collected on P28 after euthanasia. The same methodology was followed for gene deletion experiments involving conditional Vhl mice. For the specific genetic labeling of metaphyseal vasculature Cdh5(PAC)-CreERT2$^{T/+}$ mice were mated with Rosa26-mG/mT reporter line. At P29, Cdh5(PAC)-CreERT2$^{T/+}$/R26-mG/mT$^{d/+}$ mice received a single dose of 50 μg tamoxifen and were analyzed either 24 hrs (1 day) later or 40 days later.

For Rbpj deletion in the postnatal vasculature, mice carrying loxP-flanked Rbpj gene (Rbpj$^{floxed}$) were interbred with mice expressing endothelial specific tamoxifen inducible CreERT2 i.e. Cdh5(PAC)-CreERT2. The males with genotype Rbpj$^{floxed/floxed}$ Cdh5(PAC)-CreERT2$^{T/+}$ were interbred with Rbpj$^{floxed/floxed}$ females to generate litters with Rbpj$^{floxed/floxed}$ Cdh5(PAC)-CreERT2$^{T/+}$ (Rbpj$^{i\Delta EC}$) and Rbpj$^{floxed/floxed}$ (control) genotypes. To induce Cre activity and gene deletion, all the litters were injected with 500 μg tamoxifen (Sigma, T5648) intraperitoneally everyday from P10 to P14. Femur and tibia were collected from these animals for analysis on P28 after euthanasia. The same methodology was followed for all gene deletion experiments of Fbxw7 $^{i\Delta EC}$, Dll$^{i\Delta EC}$, Dll4$^{i\Delta EC}$, Jag1$^{i\Delta EC}$ and Rbpj$^{i\Delta OB}$. For osteoblast specific loss of function experiments, Col1$\alpha$1-CreERT2 mice (embryos purchased from Institut Clinique de la Souris, France) were interbred with Rbpj$^{floxed/floxed}$ mice. Further, Rbpj floxed/floxed Col1a1-CreERT2$^{T/+}$ males were interbred with Rbpj$^{floxed/floxed}$ females to generate litters with Rbpj$^{floxed/floxed}$ Col1aCreERT2$^{T/+}$ (Rbpj$^{i\Delta OB}$) and Rbpj$^{floxed/floxed}$ (control) genotypes.

For Fbxw7 deletion in the vasculature of aged mice carrying loxP-flanked Fbxw7 gene, Fbxw7$^{floxed}$ conditional mice were interbred with transgenic mice expressing endothelial specific tamoxifen inducible CreERT2, i.e. Cdh5 (PAC)-CreERT2. The males with genotype Fbxw7$^{floxed/floxed}$ Cdh5(PAC)-CreERT2$^{T/+}$ were interbred with Fbxw7$^{floxed/floxed}$ females to generate litters with Fbxw7$^{floxed/floxed}$ Cdh5(PAC)-CreERT2$^{T/+}$ (Fbxw7$^{i\Delta EC}$) and Fbxw7$^{floxed/floxed}$ (control) genotypes. To induce Cre activity and gene deletion, all the mice ranging in age between 55 to 65 weeks were injected with 1000 μg tamoxifen (Sigma, T5648) intraperitoneally every day for 5 days. After this first schedule, a time gap of 16 days was given and the mice were subjected to second round tamoxifen injections. Again in this second round of tamoxifen injections mice were intraperitoneally injected everyday for 5 days with 1000 μg tamoxifen. Following a time gap of 16 days after second round of tamoxifen injections, femurs and tibiae were collected from these animals for analysis after euthanasia.

To over express NICD in the postnatal vasculature, mice carrying LoxP-flanked stop codon blocking the expression of NICD (Gt(ROSA)26Sor$^{tm1(Notch1)Dam/J}$) were interbred with Cdh5(PAC)-CreERT2 mice. The NICD$^{+/OE}$ Cdh5 (PAC)-CreERT2$^{T/+}$ males were interbred with NICD$^{+/OE}$ females to generate littermates with NICD$^{+/OE}$ Cdh5(PAC)-CreERT2$^{T/+}$ (NICD$^{iOE-EC}$) and NICD$^{+/OE}$ Cdh5(PAC)-CreERT2$^{+/+}$ (control) genotype. To generate endothelial double mutants (Dll4$^{i\Delta EC}$/NICD$^{iOE-EC}$), Dll4$^{floxed}$ mice were first interbred with NICD$^{+/OE}$ and Cdh5(PAC)-CreERT2 mice. Dll4$^{floxed/+}$NICD$^{+/OE}$ Cdh5(PAC)-CreERT2$^{T/+}$ males were interbred with Dll4$^{floxed/+}$ NICD$^{+/OE}$ females to generate Cdh5(PAC)-CreERT2$^{+/+}$ (control), Dll4$^{floxed/floxed}$NICD$^{+/OE}$ Cdh5(PAC)-CreERT2$^{T/+}$ (Dll4$^{i\Delta EC}$/NICD$^{iOE-EC}$), Dll4$^{floxed/floxed}$ NICD$^{+/+}$ Cdh5(PAC)-CreERT2$^{T/+}$ (Dll4$^{i\Delta EC}$) and Dll4$^{+/+}$ NICD$^{+/OE}$ Cdh5(PAC)-CreERT2$^{T/+}$ (NICD$^{iOE-EC}$) mice.

For experiments involving Noggin treatment, both control and Rbpj$^{i\Delta EC}$ mice were injected intraperitoneally once daily with 500 μg/kg recombinant Noggin (1967-NG, R&D Systems) dissolved in PBS in a volume of 50 μl per dose. Another set of control and Rbpj$^{i\Delta EC}$ mice was injected with 50ul PBS for experimental control. All protein injections were done from P15 to P27, after tamoxifen treatment (P10-P14) before the day of analysis (P28).

All animals were routinely genotyped using respective PCR protocols. Protocols and primer sequences can be provided upon request. All the animals were housed in the Institute animal facility at the Max Planck Institute for Molecular Biomedicine. All experiments were performed according to the institutional guidelines and laws, following the protocols approved by local and national animal ethics committees.

Bone Immunohistochemistry

Freshly dissected bone tissues collected from wild-type mice or from mutants and their control littermates were immediately fixed in ice-cold 4% paraformaldehyde solution for 4 hrs. Decalcification was carried out with 0.5M EDTA at 4° C. with constant shaking and decalcified bones were immersed into 20% sucrose and 2% polyvinylpyrrolidone (PVP) solution for 24 hr. Finally, the tissues were embedded and frozen in 8% gelatin (porcine) in presence of 20% sucrose and 2% PVP. For immunofluorescent stainings and morphological analyses, sections were generated using low-profile blades on a Leica CM3050 cryostat.

For phenotypic analysis, mutant and littermate control samples were always processed, sectioned, stained, imaged and analysed together at the same conditions and settings. For immunostaining, bone sections were air-dried, permeabilised for 10 min in 0.3% Triton X-100, blocked in 5% donkey serum at room temperature for 30 min, and probed with the primary antibodies diluted in 5% donkey serum in PBS for 2 hr at room temperature (RT) or overnight at 4° C.

Following are the details of primary antibodies used: Endomucin (sc-65495, Santa Cruz) used at 1:100 dilution; Pecam1 conjugated to Alexa fluor 488 (FAB3628G, R&D Systems) used at dilution 1:100; Pecam1 (553370, BD Pharmingen) used at 1:100 dilution; Osterix (sc-22536-R, Santa Cruz) used at dilution 1:200; Runx2 (MAB2006, R&D Systems) used at dilution 1:200; alpha SMA-Cy3 (C6198, Sigma) used at dilution 1:100; Hif1α (ab65979, Abcam) used at dilution 1:100; Collagen type 1 (AB675P; Millipore); Osteopontin (AF808, R&D Systems) used at dilution of 1:200, Mct4 (sc-50329 Santa Cruz) used at dilution of 1:100 and Glut1 (07-1401, Millipore) used at dilution of 1:100, NG2 Chondroitin Sulphate Proteoglycan (AB5320, Millipore) used at a dilution of 1:100.

After primary antibody incubation, sections were washed with PBS for three times and incubated with appropriate Alexa Fluor-coupled secondary antibodies (1:400, Molecular Probes) for 1 hr at RT. Nuclei were counterstained with DAPI. Sections were thoroughly washed with PBS before mounting them using FluoroMount-G (Southern Biotech). Finally, cover slips were sealed with nail polish.

Calcein Double Labeling

Calcein double labeling was performed to calculate mineral apposition rate (MAR).

Mice were given intraperitoneal injections of 10 mg/kg calcein (Sigma, C0875) dissolved in 2% sodium bicarbonate solution at 10$^{th}$ day and 3$^{rd}$ day before euthanasia. Bones were fixed in 4% PFA, embedded in 8% gelatin and 2% PVP and cryosectioned. Single plane images were acquired from the sections using LSM 780 (Carl Zeiss). Mineral Apposition Rate (MAR) is the amount of bone formed during a particular time interval. It is calculated using the distance between the midpoints of two labels divided by time interval (7days).

For visualizing vascular lumina in the angiogenic front, tetramethyl rhodamine conjugated fixable dextran of 2,000, 000MW (Invitrogen, D7139) was perfused through the heart of deeply anaesthetized mice. Mice were sacrificed after 10 min and bones were processed further.

For metabolically labeling with the hypoxia probe pimonidazole (Pimo, Hypoxyprobe Inc.), mutant and control mice were intraperitoneally injected with 60 mg/kg Pimo for 2 h before euthanasia. Metabolized Pimo was detected by a rabbit antiserum against the non-oxidized, protein-conjugated form of pimonidazole (Hypoxyprobe Inc.).

DFM Treatment

For DFM treatment, freshly prepared deferoxamine mesylate (Sigma) in water was injected intraperitoneally every alternate day at the dose of 15 mg/ml per mouse over four weeks. For μ-CT analysis, this treatment was continued for five weeks. Animals in the control group were injected with same amount of sterile water.

EdU Labeling

For labelling proliferating cells, mice were intraperitoneally injected with 1.6 mg/kg weight of EdU (Invitrogen) 2 hrs before euthanasia. Tibiae were immediately collected and processed as mentioned earlier. The bone marrow cells and the bone sections were immunostained for EDU using Click-iT chemistry following the manufacturer's instructions (Invitrogen).

Image Acquisition, Quantitative Analysis and Statistics

Immunofluorescent stainings were analysed at high resolution with a Zeiss laser scanning confocal microscope, LSM-780. Z-stacks of images were processed and 3D-reconstructed with Imaris software (version 7.00, Bitplane). Imaris, Photoshop and Illustrator (Adobe) software was used for image processing. All data are presented as mean±s.e.m. The significance of difference in the mean values was determined using two-tailed Student's t test unless indicated otherwise. P<0.05 was considered significant. All calculations were performed using Graphpad Prism software.

Culture of Endothelial Cells from Bone

Tibiae and femurs from wild-type mice or mice expressing endothelial specific reporters (Flk1 GFP and Cdh5 mtmg mice) or wild-type mice were collected in sterile $Ca^{2+}$ and $Mg^{2+}$ free PBS, crushed with mortar and pestle, digested with Collagenase A (Sigma) to obtain a single cell suspension. ECs were then MACS sorted using endomucin antibody (cat. no. SC-65495) and Dynabeads sheep anti-Rat IgG (Invitrogen). Sorted ECs were then plated on dishes coated with fibronectin and cultured in endothelial cell growth medium (EBM-2, Clonetics; Lonza) supplemented with EGM-2 SingleQuots (CC-4176, Clonetic; Lonza). At first passage, cells were again MACS sorted with endomucin antibody and plated for culture. Cells were fed every third day and passaged upon confluency. Cultures were maintained at 37° C. with 5% CO2 in a humidified atmosphere. For DFM treatment and subsequent qPCR analysis, EC cultures between passage 2 and 5 were used. Cells were treated with DFM 6.25 mg/ml of culture medium for the duration of 7 hrs and subsequently lysed in lysis buffer of RNeasy Mini Kit (QIAGEN) for qPCR analysis.

Quantitative RT-PCR

For the analysis of mRNA expression levels in type H or type L endothelium, $CD31^{hi}/Emcn^{hi}$ and $CD31^{lo}/Emcn^{lo}$ cells were sorted by FACS directly into the lysis buffer of the RNeasy Mini Kit (QIAGEN). Total RNA was isolated according to manufacturer's protocol. A total of 100 ng RNA per reaction was used to generate cDNA with the iScript cDNA Synthesis System (Bio-Rad). Quantitative PCR (qPCR) was performed using TaqMan gene expression assays on ABI PRISM 7900HT Sequence Detection System. The FAM-conjugated TaqMan probes Tgfb1, Tgfb3, Fgf1, Pdgfa, Pdgfb and Kitl were used along with TaqMan Gene Expression Master Mix (Applied Biosystems). Gene expression assays were normalized to endogenous VIC-conjugated Actb probes as standard. For analysis of mRNA expression levels from whole bones, dissected femurs were immediately crushed finely, digested with collagenase, centrifuged to obtain a pellet, which was then lysed into lysis buffer of RNeasy Mini Kit (QIAGEN). A total of 500 ng RNA per reaction was used to generate cDNA with the iScript cDNA Synthesis System (Bio-Rad), which was further processed as described above. FAM-conjugated TaqMan probes Ibsp, Bglap, Sp7, Cspg4, Pdgfrb, Runx2, and Sp7 were used along with TaqMan Gene Expression Master Mix (Applied Biosystems) to perform qPCR. For the mRNA expression analysis of flushed bone and bone collar/endosteum, FAM-conjugated TaqMan probes Tgfb1, Tgfb3, Fgf1, Pdgfa, and Pdgfb were used. Gene expression was normalized to the endogenous VIC-conjugated Actb probes.

For the analysis of mRNA expression levels, pure total bone endothelial cells were flow-sorted directly into the lysis buffer of RNeasy Mini Kit (QIAGEN). Total RNA was isolated according to manufacturer's protocol. A total of 100-500 ng RNA per reaction was used to generate cDNA with the iScript cDNA Synthesis System (Bio-Rad). Quantitative PCR (qPCR) was performed using TaqMan gene expression assays on ABI PRISM 7900HT Sequence Detection System. The FAM-conjugated TaqMan probes Tgfb1, Tgfb2, Tgfb3, Bmp2, Bmp4, Nog, Chrd, Cert, Fgf1, Fgf8, Wnt1, Wnt3a, Wnt5a, Wnt10b, Dkk1 were used along with TaqMan Gene Expression Master Mix (Applied Biosystems) to perform qPCR. Gene expression assays were normalized to the endogenous VIC conjugated Actb probes as control. For analysis of Bgalp, Ibsp Cspg4, and Pdgfrb expression, RNA was isolated from the whole bone samples of mutants and their littermate control animals. Freshly dissected femurs were immediately crushed and lysed in lysis buffer. RNA isolation, cDNA preparation and qPCR were done as mentioned earlier.

Flow Cytometry

For flow cytometric analysis and sorting of type H and type L ECs, tibiae and femurs were collected, cleaned thoroughly to remove the adherent muscles. The epiphysis was removed and only the metaphysis and diaphysis regions were processed. Tibias were then crushed in ice cold PBS with mortar and pestle. Whole bone marrow was digested with collagenase incubation at 37° C. for 20 min. Equal number of cells were then subjected to immunostaining with endomucin antibody (Santa cruz, sc-65495) for 45 min. After washing, cells were stained with APC-conjugated CD31 antibody (R&D Systems, FAB3628A) for 45 min. After washing, cells were acquired on BD FACS Canto flow cytometer and analysed using BD FACSDiva software (Version 6.0, BD Bioscience). Cell sorting was performed with FACS Aria II. For demarcating and sorting $CD31^{hi}/Emcn^{hi}$ ECs, first standard quadrant gates were set, subsequently to differentiate $CD31^{hi}/Emcn^{hi}$ cells from the total double positive cells in quadrant 2 gates were arbitrarily set at $>10^4$ log Fl-4 (CD31-APC) fluorescence and $>10^4$ log Fl-2 (Endomucin-PE) fluorescence.

Bone marrow cells were isolated by crushing the long bones with mortal and pestle in chilled $Ca^{2+}$ and $Mg^{2+}$ free PBS with 2% heat-inactivated bovine serum. The following antibodies were used to stain HSCs: CD150 (SLAM) Alexa-488 (MCA2274A488, AbD Serotec), anti-CD48 (NBP1-76556, Novus Biologicals), Lineage Cocktail mouse AlexaFluor700 (133313, BioLegend), CD117-APC (c-Kit) (553356, BD Pharmingen), CD117-APC (c-Kit) (553356, BD Pharmingen). DAPI was used to exclude dead cells.

For the analysis of total ECs in bone, tibiae were processed as described above to obtain single cell suspensions, which were stained with biotin-coupled Cd45 (BD, 553077) or Ter119 (BD, 559971) antibodies for 45min. After washing in PBS, cells stained with Streptavidin PE-Cy5 (BD, 554062) and Alexa Fluor488-conjugated CD31 (R&D Systems, FAB3628G) antibodies for 45 min. After washing, cells were acquired on a FACS Canto flow cytometer and analysed using FACSDiva software (Version 6.0, BD Bioscience).

RNA Extraction and Microarray Hybridization

Total RNA was isolated from freshly isolated bone endothelial cells using the Qiagen RNeasy minikit (Qiagen, Inc.) according to the manufacturer's protocol. Microarray hybridization was carried out at Arrows Biomedical Deutschland GmbH. Samples were labeled using the Agilent Low Input RNA amplification kit and were hybridized to Agilent Mouse Whole Genome 4×44k Mouse v2 Array using the Agilent In situ Hybridiztion kit.

Micro-CT Analysis and Electron Microscopy

Tibiae were collected, and the attached soft tissue was removed thoroughly and fixed in 4% paraformaldehyde. The fixed tibiae were analyzed using micro-CT (µCT 35) and software IPL V5.15 at Scanco Medical AG, Switzerland. A voxel size of 12 µm was chosen in all three spatial dimensions. For each sample, 148 from 232 slices were evaluated covering a total of 1.776 mm at a voltage of 70kVp, intensity 114 µA, integration time 1200 ms.

Statistics

All data are presented as mean±s.e.m. The significance of difference in the mean values was determined using two-tailed Student's t test unless otherwise mentioned. P<0.05 was considered significant. In others, Non-parametric one-way ANOVA was performed along with Bonferroni's multiple comparison post-test to assess statistical significance with a 95% confidence interval. All calculations were performed using Graphpad Prism software.

Example 1

Visualization of Bone Vasculature at High Resolution to Show Vessel Architecture To characterize the organization of arteries, a-smooth muscle actin (a-SMA) staining on thick sections (300 µm) of 4 week old tibia (mouse) was performed. Straight and smooth muscle cell-covered arteries entered the bone through the cortex (FIG. 2a). In the diaphysis, a few traversing, largely unbranched central arteries were seen, whereas substantial branching could be seen in the metaphysis when arteries approached the growth plate (FIG. 2a). Analysis of the distal arterioles revealed that few of these vessels terminated at capillaries in the endosteum (i.e. the connective tissue lining the inner surface of compact bone), whereas most branch and termination points were found in the metaphysis in proximity of the growth plate (FIG. 2b, c).

Example 2

Examination of Implications for Bone Oxygenation

To examine whether the spatial pattern of artery-capillary connections affected the metabolic status of the surrounding tissue analysis of hypoxia-inducible factor 1-α (HIF1-α) was carried out. HIF1-α immunostaining on sections of 7 week old tibiae (mouse) showed abundant staining of cell nuclei throughout the diaphysis and in secondary ossification centers, but not in the metaphysis.

Tibia sections from 7 week old mice were immunostained for MCT4 and Glut1. Maximum intensity projections thereof showed that the plasma membrane lactate transporter MCT4, a hypoxia-regulated protein and the glucose transporter-1 (Glut1), which is induced by HIF signaling and low glucose levels, were also abundant throughout the diaphysis, while antibody signals were weak or absent in the metaphysis. These data suggest that regional differences in oxygenation and metabolic activity in long bone are determined by the spatial distribution of distal arteries and, in particular, the total abundance of arteriole-capillary connection points in the metaphysis.

Example 3

Identification of a Distinct Endothelial Cell Subpopulation in Bone by Visualization of Vasculature Using Fluorescent Reporter of Endothelial Specific Cre Activity in Transgenic Mice The bone vasculature was visualized using a combination of endothelial cell specific, tamoxifen-inducible Cdh5 (PAC)-CreERT2 and Rosa26-mT/mG Cre reporter transgenic mice (GFP+ endothelium). Tile scan confocal imaging Cdh5(PAC)-CreERT2 of 4 week old tibiae uncovered the existence of structurally and spatially distinct capillary subsets. Endothelial tubes in the metaphysis were arranged in straight and columnar strands, which were interconnected at their distal ends by looping vessels or arches (see FIG. 10a). In contrast, microvessels in the diaphysis displayed the irregular, highly branched and interconnected pattern of vessels characteristic for the sinusoidal vasculature of bone marrow (see FIG. 10a). At the interface between metaphysis and diaphysis, the two structurally and spatially distinct vessel types were connected confirming that they were part of one, continuous vessel bed (FIG. 10a).

Example 4

Identification of a Distinct Endothelial Cell Subpopulation in Bone by Immunostaining Different immunostainings of 4 week old tibiae were carried out and analyzed using confocal tile scan images.

The columnar tubes and distal arch vessels in the metaphysis and endothelial cells in the endosteum were strongly positive for the marker CD31/PECAM1 and Endomucin (Emen), while the irregular, sinusoidal vessels in the diaphysis displayed substantially lower expression of CD31. Furthermore, Endomucin expression was also slightly lower in these vessels (FIG. 3a and FIG. 10b). A distinct $CD31^{hi}/Emcn^{hi}$ endothelial subset could be also identified and separated from $CD31^{lo}/Emcn^{lo}$ cells in single cell suspensions of long bone (FIG. 3b). Analysis of arteries in relation to the two microvascular subsets indicated that distal arterioles, which were CD31+ but lacked endomucin expression, always terminated within the $CD31^{hi}/Emcn^{hi}$ endolhelium (FIG. 2b). Qualitative analysis of the different EC populations by flow cytometry showed that $CD31^{hi}/Emcn^{hi}$ subsets represented only a small fraction of the total bone marrow endothelium in adult mice (FIG. 3c).

Thus the comparison of different immunostainings showed that it is possible to distinguish different vessel types and capillary subsets with specific cell surface marker. Said observations establish the existence of structural, spatial and phenotypic heterogeneity in the bone endothelium. These findings not only apply to long bones, but also to other skeletal elements such as vertebra, sternum and calvarium in mice (Suppl. FIG. 4a-c). The analysis of EC from other organs for CD31 and Endomucin expression showed that they all, with the exception of liver, lacked a comparable $CD31^{hi}/Emcn^{hi}$ endothelial subset (FIG. 11). On the basis of these findings the following terminology for the endothelium of bone microvessels is used herein: type H for the small $CD31^{hi}/Emcn^{hi}$ subset and type L for the $CD31^{lo}/Emcn^{lo}$ cells of the irregularly shaped, sinusoidal vessels in the diaphysis.

Example 5

Examination of Structures Suitable for Bone Angiogenesis

Sections of 4 week old tibia were immunostained with antibodies against Osterix as marker for osteoblastic cells and CD31 for endothelial cells. These immunostaining visualized endothelial columns, which are straight and sparsely branched tubules with a diameter of around 5-10 µm. At their distal end in direct proximity of growth plate chondrocytes, these columns are linked by tubular loops (i.e. arches), which also carried interconnecting side branches and blindended bulb-shaped protrusions with a caliber of around 15-20 µm. Osterix-positive osteoblasts and their progenitors were abundant around the endothelial columns, but were absent around the distal arches. Arch vessels extended filopodia towards the growth plate, but, based on confocal imaging and transmission electron microscopy, lacked tip cells and sprouts (cf. FIG. 16).

Perfusion with dye-labelled Dextran and expression of lumen markers like ICAM2 or Podocalyxin demonstrated that unlike endothelial sprouts, distal arch vessels and their protrusions were lumenised. Electron micrographs also showed fully lumenised vessels in direct proximity of hypertrophic chondrocytes.

To determine how endothelial cell proliferation contributes to the expansion of metaphyseal vessel EdU labeling of dividing cells was performed. This revealed that endothelial proliferation predominantly occurred within columns and, to lesser extent, in distal arches (FIG. 14a). CD31+ Endomucin-arterioles terminate in the distal vascular arches which are positive for both CD31 and Endomucin (FIG. 14b; $CD31^{hi}/Emcn^{hi}$.

Example 6

Evaluation of Spatial Relationship Between Type H Endothelium and Localization of Osteoprogenitor Cells The discovery of two distinct capillary endothelial subsets in bone raised the question whether this relates lo functional heterogeneity. Evaluation of the spatial relationship between vessels and Osterix-positive osteoprogenitors showed that these cells, which will give rise to osteoblasts and osteocytes, were selectively positioned around type H but not type L endothelium (see also example 5).

Likewise, further immunostaining of 4 week old tibiae, revealed that collagen type 1α expressing cells of the osteoblast lineage as well as Runx2-positive early osteoprogenitors were abundant around the CD31+ columnar endothelial tubes in the metaphysis and in proximity of the CD31+ endosteal endothelial cells, but virtually absent from the vicinity of type L vessels in the diaphysis. Quantization showed that, despite the low frequency (~1.77%) of type H endothelial cells in the bone endothelial cell fraction and ~0.015% in total bone marrow (FIG. 3b), the majority of Runx2+ (82.63±18%), collagen 1α+ (74±3.3%) and Osterix+ cells (70±1.9%) were located directly adjacent to $CD31^{hi}/ECmn^{hi}$ vessels (FIG. 4). Mesenchymal cells expressing platelet-derived growth factor receptor β (PDGFRβ), a receptor tyrosine kinase, were also found associated with type H vessels in metaphysis and endosteum as well as arteries, but were comparably less around type L endothelium.

Example 7

Growth Factor mRNA Expression of Isolated $CD31^{hi}/ECmn^{hi}$ Cells

To identify molecular properties of $CD31^{hi}/ECmn^{hi}$ endothelial cells that might explain the preferential association of osteoblastic cells, type H and type L endothelial cells were purified from long bone, and the expression of mRNAs for secreted growth factors with known roles in the survival and proliferation of osteoprogenitors was analyzed by quantitative PCR (qPCR). This revealed significantly higher expression of Pdgfa, Pdgfb, Tgf1, Tgf3, and Fgf1 transcripts in type H endothelial cells relative to type L cells (FIG. 5a) Likewise, qPCR analysis of flushed tibiae, in which the endosteal type H endothelium was retained revealed a strong enrichment of the same transcripts in comparison to the extracted marrow containing type L endothelial cells. These data show that the two subsets of bone capillary endothelial cells have specific expression profiles, which, in turn, suggested specialized functional properties.

Example 8

Determination of the Amount of Type H Endothelium During Aging

It has been previously reported that the number of osteoblast declines upon aging. As a consequence of reduced osteogenesis, bone quality and fracture healing deteriorate with age.

On representative confocal images from metaphyseal and diaphyseal regions of tibias from mice of different ages immunostained for Osterix and CD31 a remarkable decline in osteoprogenitor cells in long bone of aging mice was observed (FIG. 12a). This was accompanied by a significant decrease in the transcript levels of markers far early mesenchymal progenitors and osteoprogenitors (FIG. 12b) as well as the loss of bone mass. Remarkably, these changes correlated with pronounced age-dependent reduction of type H vessels, which were much more abundant in juvenile (4 week-old) mice compared to (11 week-old) adults, and were nearly absent in aged (70 week-old) animals (FIG. 5b, FIG. 12a).

Flow cytometry analysis confirmed this age-dependent reduction of $CD31^{hi}/Emcn^{hi}$ endothelial cells, whereas the total number of bone endothelial cells did not show significant changes (FIG. 5c; FIG. 13a). Suggesting that type H endothelium might be linked to angiogenic vessel growth, ECs proliferation was prominently associated with the type H subpopulation in 4 week-old mice and declined rapidly in adulthood (FIG. 5d; FIG. 13a, b). In contrast, the rate of proliferation seen in juvenile type L endothelial cells did not change significantly in older animals (FIG. 6d). While flow cytometry data suggest the existence of a potential $CD31^{hi}/Emcn^{hi}$ endothelial cell subpopulation in liver the fraction of these cells did not decline in adult and aged mice (FIG. 13c). The proliferation data pointed at a potential role of type H endothelium in the angiogenic growth of the vasculature in bone.

Example 9

Evaluation of Relationship Between Type H Endothelium and Neo-Angiogenesis in Bone by Genetic Lineage For genetic lineage tracing 4 week-old Cdh5(PAC)-Cre-ERT2×ROSAZ6-mT/mG double transgenic mice were once injected a low dose of tamoxifen (see Methods above). This led to highly selective green fluorescent protein (GFP) expression in metaphyseal and endosteal type H endothelium cells as well as in the endothelium of CD31+ arteries (FIG. 6a). The analysis of mice at day 40 after tamoxifen administration (i.e., a 9.7 weeks of age) revealed a profound expansion of the GFP-positive endothelial cells, which were abundant not only in the metaphysis but also throughout the diaphysis (FIG. 6a). As the latter contains $CD31^{lo}/Emcn^{lo}$ vessels, this finding establishes that type H endothelium cells can give rise to type L endothelium. This, together with the high proliferative capacity of the CD31$^{hi}$/Emcn$^{hi}$ fraction, shows that the small subset of type H endothelial cells has special growth properties and is hierarchically upstream of the majority of the bone sinusoidal (type L) endothelium.

Example 10

Analysis of Dynamics of Endothelial Subsets after Irradiation

Exposure to irradiation is known to induce regression of sinusoidal endothelium, and a transient but substantial decline in endothelial cell number. Therefore flow cytometric quantifications based on CD31 and Endomucin double staining at 7 days post irradiation were performed and a significant increase in the number of type H endothelial cells was found and, concomitantly, strong reduction of the type L subpopulation (FIG. 6b). Likewise, immunostaining of tibia sections showed the presence of CD31$^{hi}$/Emcn$^{hi}$ vessels throughout the diaphysis (FIG. 6b). The sum of the findings of examples 9 and 10 argues for a role of CD31$^{hi}$/Emcn$^{hi}$ endothelial cells in developmental and, presumably, regenerative neo-angiogenesis in bone.

Example 11

Investigation of the Role of HIF by Loss-of-Function Observation after Endothelial Cell-Specific Gene Deletion Inducible endothelial cell-specific loss-or-function mice (Hif1α$^{i\Delta EC}$) were generated by combining conditional, loxP-flanked Hif1α alleles (Hif1α$^{lox/lox}$) and the Cdh5 (PAC)-CreERT2 transgene. Following tamoxifen administration from postnatal day (P) 10 to P14 analysis of bone vasculature in the resulting Hif1α$^{i\Delta EC}$ mutants at postnatal day 20 (P20) revealed striking vessel subtype-specific effects. While type H endothelium was strongly reduced in the metaphysis and endosteum, diaphyseal type L vessels were unaffected and comparable to control littermates (FIG. 6c). This reduction of type H endothelial cells in Hif1α$^{i\Delta EC}$ long bone was also confirmed by flow cytometry.

The von Hippel-Lindau (VHL) tumor suppressor is an E3 ubiquitin protein ligase that controls the stability and thereby biological activity of HIF-1α and other substrates. Inducible targeting of the murine Vhl gene in postnatal endothelial cells with the same strategy as for Hif1α$^{i\Delta EC}$ led Ia the pronounced expansion of type H endothelium and, in particular, the endothelial columns in the metaphysis (FIG. 6d). These changes were accompanied by noticeable expansion of the metaphysis and increased formation of trabecular bone in Vhl$^{\Delta EC}$ mutants. Likewise, a significant increase in the number of Runx2+ osteoprogenitors and Osterix+ cells was observed in long bone (FIG. 6b). Conversely, these cell types were significantly reduced in Hif1α$^{i\Delta EC}$ samples (FIG. 9a).

Example 12

Investigation of the role of HIF by pharmacological stabilisation of Hif1α

Prolyl-4-hydroxylases (PHDs) modify Hif1α and thereby mark the protein for degradation under normoxic conditions. Accordingly, administration of PHD inhibitors such as deferoxamine mesylate (DFM) enhances Hif1α stability and activity.

Therefore isolated primary bone endothelial cells were treated (see Methods) with DFM and could observe not only up regulation of the transcripts for CD31 and Endomucin, but also an increase in the expression of growth factor mRNAs, namely Pdgfa, Pdgfb, Fgf1, Tgfb1, Tgfb3 (FIG. 9b). Notably, these transcripts were also highly enriched in freshly isolated CD31$^{hi}$/Emcn$^{hi}$ endothelial cells (FIG. 10a).

The observations of example 11 and 12 together with the age-related decline of CD31$^{hi}$/Emcn$^{hi}$ endothelial cells and bone mass raised the question whether it is possible to induce neo-angiogenesis and osteogenesis in aged animals with DFM. While long bones of aged, 64 to 70 week-old mice treated with vehicle control contained very few CD31$^{hi}$/Emcn$^{hi}$ vessels, DFM administration (see Methods) lead to substantial expansion of type H endothelium (FIG. 8a). This was accompanied by the emergence of Osterix-positive cells in tight association with type H vessels (FIG. 8b). Expression levels of mRNAs for molecular markers for osteoprogenitors and osteoblasts, namely Sp7 (encoding Osterix), Bglap (bone gamma-carboxyglutamate protein) and Ibsp (integrin-binding sialoprotein), were significantly increased in long bone of DFM-treated animals. Furthermore, μ-CT examination showed that 6 weeks of DFM treatment led to significant increase in bone mass compared to aged control mice (FIG. 9 c,d). The sum of these findings highlight crucial roles of endothelial HIF in the regulation of bone angiogenesis, the abundance of type H vessels, the expression of secreted growth factors by endothelial cells, and osteogenesis.

Example 13

Investigation of the Role of Notch Pathway by Phenotypic Observation After Endothelial Cell-Specific Gene Targeting The Notch pathway is an important negative regulator of angiogenesis in many model systems, thereby Notch and Delta-like 4 (Dll4), which signal in a cell-cell contact-dependent fashion between endothelial cells, suppress excessive tip cell formation and mitogenic activity in the growing vasculature. Inducible targeting of the Rbpj gene encoding RBP-JK, an essential mediator of Notch-induced gene transcription, was performed using Cdh5(PAC)-CreERT2 transgenic mice in the postnatal endothelium which led to an unexpected decrease in the number of Endomucin+ vessels and reduction of total as well as proliferating (EdU-labeled) endothelial cells in long bone (FIG. 15). The pattern of distal vascular columns and arches was disrupted in Rbpj$^{i\Delta EC}$ tibiae, and mutant vessels were dilated, irregular and disorganized.

For Notch-gain-of-function experiments, the Fbxw7 gene was first targeted, which encodes a key component of the SCF protein complex responsible for the polyubiquitination and proteasomal degradation of active Notch receptors, with an inducible endothelial cells-specific strategy. While Fbxw7$^{i\Delta EC}$ mutants were recently shown to have strongly reduced angiogenesis in the retina due to Notch overactivation, distal column and arch structures were more abundant in mutant long bone, and the number of total and EdU+ endothelial cells was significantly increased (FIG. 15).

As Fbxw7 controls the degradation of other substrates besides Notch, also mutants overexpressing the Notch intracellular domain (NICD) in a Cdh5(PAC)-CreERT2-dependent fashion in endothelial cells were analyzed. Phenocopying the Fbxw7$^{i\Delta EC}$ results, expression of active NICD led to the pronounced expansion of the CD31+ Endomucin+ vessels in the metaphysis of postnatal long bone. Thus while Notch is an important negative regulator of vessel growth and endothelial proliferation in other organs, the pathway positively controls angiogenesis in the skeletal system.

Defective angiogenesis in endothelial cell-specific Rbpj$^{i\Delta EC}$ mice was accompanied by decreased size of mutant long bones at 4 weeks of age (FIG. 16a). Hematoxylin-eosin staining of Rbpj$^{i\Delta EC}$ bone sections revealed defective organization of the metaphysis with large, irregular lacunae (FIG. 16b). Immunostaining for osteopontin a secreted bone sialoprotein, showed that the mutant metaphysis lacked clearly separated trabeculae and contained numerous small, irregularly arranged and highly interconnected trabecular elements (FIG. 16c). Three-dimensional reconstruction of tibia using micro-computed tomography (μCT) confirmed a significant loss of bone mass in Rbpj$^{i\Delta EC}$ mutants and reduced bone density (i.e., bone volume over total volume; BV/TV) (FIG. 16d, e). Endothelial targeting of Rbpj also led to decreased trabecular bone thickness (FIG. 16e) and enlarged trabecular separation. When calcein double labeling was performed during an interval of 7 days before analysis at postnatal day (P) 28, Rbpj$^{i\Delta EC}$ tibiae had strongly reduced mineral apposition rates compared lo littermate controls (FIG. 16f, g). Thus, loss of endothelial Rbpj function led to pronounced bone defects.

Furthermore the status of osteoblasts and osteoprogenitors was analyzed. The number of Osterix-positive cells was significantly enlarged in the metaphysis whereas the stabilization of active Notch in Fbxw7$^{i\Delta EC}$ mice strongly reduced the number of these cells (FIG. 16h-j). Markers of mature osteoblasts .such as Bglap (bone gamma-carboxyglutamate protein) and or lbsp (integrin-binding sialopralein) were expressed at lower levels in Rbpj$^{i\Delta EC}$ bows (FIG. 16k) which suggested that the accumulating Ostrix+ cells represented immature osteoblasts. Conversely, Runx2-positive early osteoprogenitors, immature cells that give rise to osteoblasts were strongly reduced in Rbpj$^{i\Delta EC}$ samples (FIG. 16l,m) but more abundant in Fbxw7$^{i\Delta EC}$ mutants (FIG. 16n)

To gain further insight into the differentiation of osteoprogenitors, mesenchymal cells from Rbpj$^{i\Delta EC}$ and littermate control bones were isolated and differentiated in vitro into cells of the osteoblast lineage. Mesenchymal cells from Rbpj$^{i\Delta EC}$ mice generated mineral nodules within 10-14 days and thereby substantially earlier than control samples, which contained nodules only after 21-28 days. This finding is consistent with the profound accumulation of Osterix+ osteoprogenitors after endothelial cell-specific ablation of the Rbpj gene (FIG. 16h). Together, these data suggest that the differentiation of osteoprogenitors in the hone is regulated by endothelial cell-derived signals and depends on the status of endothelial Notch signaling.

Example 14

Identification of the Relevant Notch Ligand using Transgenic Mice

Next a series of endothelial cell-specific mutant mice was generated to identify the relevant Notch ligand in the bone endothelium. For this purpose, Cdh5(PAC)-CreERT2 transgenic mice were combined with conditional mice carrying loxP-flanked alleles of the Dll1, Dll4 or Jag1 (encoding Jagged1) genes, respectively. While angiogenesis or patterning of vessels was not altered in the skeleton of the resulting Dll1$^{i\Delta EC}$ or Jag1$^{i\Delta EC}$ mutants, Dll4$^{i\Delta EC}$ long bones were substantially shorter indicative of defective growth. Analysis of the Dll4$^{i\Delta EC}$ vasculature in P28 tibia by immunohistochemistry and confocal imaging showed profound structural alterations recapitulating the Rbpj$^{i\Delta EC}$ phenotype and, in particular, loss of the column/arch organization of the distal vessels in proximity of the growth plate. Likewise, Dll4$^{i\Delta EC}$ mutants phenocopied skeletal alterations seen in Rbpj$^{i\Delta EC}$ long bone such as loss of trabeculae, the formation of small and highly interconnected bony elements, and accumulation of Osterix+ cells with concomitant reduction of Runx2+ early osteoprogenitors. Thus, endothelial Dll4 is crucial for the pattering of bone vessels and osteogenesis. The striking similarities of the Dll4$^{i\Delta EC}$ and Rbpj$^{i\Delta EC}$ phenotypes also argued that RBP-JK is indeed essential for Notch signaling in bone endothelial cells and not primarily acting as a transcriptional repressor.

To address if endothelial Dll4 might signal through Notch receptors presented by perivascular mesenchymal progenitors the Rbpj gene was targeted in postnatal osteoblastic cells with Tg(Col1α1-creERT2)6.1.ICS transgenic mice (Institut Clinique de la Souris, France) during the same time period as for the endothelial cell-specific mutants introduced above. The resulting Rbpj$^{i\Delta OB}$ mutants showed no appreciable defects in the metaphyseal vasculature or in the number of Osterix+ or Runx2+ cells at P28. These results indicate that temporally restricted loss of Rbpj function in postnatal osteoblasts do not phenocopy defects observed in constitutive, non-inducible Notch pathway mutants.

To directly establish that endothelial cells function as both signal sending (i.e., ligand expressing) and signal receiving cells instead of activating Notch receptors on other cell populations, Dll4$^{i\Delta EC}$ loss-of-function and endothelial cell-specific, inducible NICD overexpressing mutants (NICD$^{iOE-EC}$) were combined. This strategy rescued the structural alterations seen in the Dll4$^{i\Delta EC}$ metaphysis and bone vasculature, enabled the formation of trabeculae, and restored the numbers of Osterix+ and Runx2+ cells close to control levels (FIG. 17). These findings demonstrate that endothelial cell-specific and cell-autonomous Notch activity regulates bone angiogenesis and couples it to osteogenesis.

Recent studies have highlighted the importance of so-called angiocrine factors that are secreted by endothelial cells to control growth and regeneration processes in the surrounding organ. To identify potential endothelial cell-derived signals acting on cells of the osteoblast lineage, endothelial cells isolated from Fbxw7$^{i\Delta EC}$ and littermate control long bones are screened for the expression of several candidate factors. This approach shows that mRNA levels for Tgfb2, Bmp4, Fgf1, Fgf8, Wnt1, Wnt3a, Wnt10b and Dkk1 are significantly increased in the Fbxw7$^{i\Delta EC}$ endothelium (FIG. 18a). However, the highest upregulation-around 40-fold compared to control endothelial cells-is observed for Nog transcripts encoding Noggin a secreted protein that binds and antagonises bone morphogenetic proteins (BMPs). In contrast, other secreted BMP antagonists such as Chordin (Chrd) and Cerberus 1 (Cert) are not expressed in FACS-isolated bone endothelial cells (FIG. 18a). Further arguing for Noggin as a Notch-controlled angiocrine regulator, purified endothelial cells from Rbpj$^{i\Delta EC}$ bones show significantly reduced Nog expression (FIG. 16b). Noggin immunostaining of control tibia sections confirm that its expression is high in the endothelial columns and distal arches in the metaphysis as well as in the perivascular cells surrounding these vessels. Noggin protein is also detectable in the diaphysis albeit at lower level and not in overt association with vascular structures. Consistent with its known role in the regulation of bone formation Noggin treatment inhibits the differentiation of primary mesenchymal cells into osteoblasts in vitro (FIG. 18c). In the presence of recombinant Noggin, mineral nodule formation (i.e., osteoblast maturation) is delayed and alkaline phosphatase expression (a feature of immature osteoprogenitors) is maintained even after 28 days of in vitro differentiation (FIG. 18c). While the full inactivation of the murine Nog gene is incompatible with embryonic development, haploinsufficient heterozygotes and osteoblast-specific mutants are reported to develop various skeletal defects including impaired bone formation, shortened femoral length and reduced number of trabeculae. As the latter changes are reminiscent of defects in endothelial cell-specific Notch pathway mutants, $Rbpj^{i\Delta EC}$ mice were injected with recombinant Noggin protein once daily for a period of 2 weeks prior to analysis of the animals at P28. Noggin treatment restores the organization of the $Rbpj^{i\Delta EC}$ metaphysis, reduces the number of Osterix+ cells to control levels, and increases the abundance of Runx2+ osteoprogenitors compared to saline-treated mutants (FIG. 18d-f, and FIG. 19a). In addition, calcein double labeling indicated that Noggin administration significantly restores bone formation and mineral apposition rates (FIG. 18g and FIG. 19b). The organization of the $Rbpj^{i\Delta EC}$ bone vasculature is partially restored by exogenous Noggin emphasizing the tight link between osteogenesis and angiogenesis (FIG. 19c). The sum of the work presented here shows that Notch and the angiocrine release of Noggin couple the specialized sub-population of h-type endothelial cells to osteogenesis.

Example 15

Endothelial Cell-specific Inhibition of Fbxw7 Reactivates CD31 hi Endothelial Cells in Bone of Aged Mice and Thereby Improves Stromal and Hematopoietic Stem Cells.

To address if the generation of type H endothelial cells is sufficient to restart angiogenesis in the skeletal system of aged mice, $Fbxw7^{floxed/floxed}$ mice carrying the Cdh5(PAC)-CreERT2 transgene and CreERT2-negative control littermates were kept to an age of 55-65 weeks without any administration of tamoxifen. At this stage, animals received two series of 5 daily tamoxifen injections each and an intermittent resting period of 16 days (FIG. 20a). After a further 16 days, animals were sacrificed and long bones were isolated for analysis. In line with previous findings in aged wild-type mice, CreERT2-negative control bones contained very few type H vessels and a small number of CD31-positive arterioles (FIG. 20b, c). By contrast, $Fbxw7^{floxed/floxed}$ Cdh5(PAC)-CreERT2 ($Fbxw7^{i\Delta EC}$) mutants showed a striking expansion of type H vasculature near the epiphyseal line and a significantly increased number of CD31-positive arterioles (FIG. 20b, c). Accordingly, flow cytometry showed that the number of endothelial cells expressing ephrin-B2 (Efnb2), a marker for type H and arterial vessels, was significantly increased in $Fbxw7^{i\Delta EC}$ mutants relative to controls (FIG. 20c). Perivascular cells stabilising vessels, as detected by immunostaining of a-smooth muscle actin (aSMA) or the proteoglycan Ng2/Cspg4, were also improved in aged $Fbxw7^{i\Delta EC}$ mutants (FIG. 20d, e). Furthermore, qPCR analysis of mutant and littermate control bone samples confirmed higher expression of transcripts for Ng2 and Pdgfrb (the gene encoding platelet-derived growth factor receptor β) and thereby argued further for an increase of perivascular mesenchymal cells after EC-specific inactivation of Fbxw7. Consistent with previous work showing that endothelial and perivascular cells form the hematopoietic stem cell (HSC) niche in bone marrow, flow cytometry showed that the improvement of type H vessels and perivascular cells in aged $Fbxw7^{i\Delta EC}$ mutants led to significantly increased number of HSCs. HSCs were determined as bone marrow cells lacking expression of lineage markers for differentiated hematopoietic cells, express the stem cell antigen Sca-1, express high levels of the SCF receptor kit, were positive for the marker CD150, and negative for CD48.

Additional work has shown that HSCs maintenance requires the expression of stem cell factor, which is encoded by the Kitl gene, by endothelial and perivascular cells. Supporting an important role of type H endothelial in stem cell factor expression, qPCR analysis of freshly isolated bone ECs from $Vhl^{\Delta EC}$ or $Fbxw7^{i\Delta EC}$ mutants or mice with an EC-specific overexpression of NICD showed significantly higher Kitl transcript levels than their littermate controls (FIG. 21a, b). Conversely, Kitl expression was significantly reduced in $Hif1a^{\Delta EC}$ or $Rbpj^{i\Delta EC}$ loss-of-function mutants (FIG. 21a, b).

Taken together, these findings show that the small subpopulation of type H ECs plays an important role in the maintenance of hematopoietic stem cells and argues that the activation of HIF or Notch signaling in the endothelium of the aged organism can be used to improve functional properties of the skeletal system, which otherwise typically decline with old age.

Example 16

Comparision of Gene Expression in Type H Bone Endothelial Cells and Type L Bone Endothelial Cells To further characterize the new subtype of bone endothelial cells the transcriptom of type H bone endothelial cells was compared to the transcriptome of type L cells. Table 2 shows selected results (See FIG. 22).

Table 2: DNA Array Data (See FIG. 22)

Gene expression heat map of selected genes with higher expression in type H ($CD31^{hi}/Emcn^{hi}$) ECs (hi1 or hi2) relative to type L ($CD31^{lo}/Emcn^{lo}$) ECs (lo1 or lo2) freshly sorted from murine long bone. Analysis was performed by hybridization with Affymetrix mouse DNA array. Shown are gene names (column 1), mean expression values (columns 2-5) and fold changes calculated by dividing the average mean values for hi1/2 by those for lo1/2 samples. Dark coloring of the cells represents higher and light grey or white lower expression.

The invention claimed is:

1. A method for generating a type H bone endothelial cell comprising contacting an isolated bone endothelial cell with a Pollyl-4hydroxylase inhibitor thereby generating a type H bone endothelial cell from the isolated bone endothelial cell.

2. The method of claim 1, wherein contacting the isolated bone endothelial cell with the Prolyl-4-hydroxylase inhibitor increases the stability or biological activity of HIF-1α in said isolated bone endothelial cell.

3. The method of claim 1, wherein contacting the isolated bone endothelial cell with the Prolyl-4-hydroxylase inhibitor mediates bone angiogenesis and osteogenesis.

4. The method of claim 1, wherein the Prolyl-4-hydroxylase inhibitor is present in an amount from 10 ng/g to 1000μg/g.

5. The method of claim 1, wherein the isolated bone endothelial cell is a type L bone endothelial cell.

6. A method of promoting bone health in a subject comprising:
- generating a type H bone endothelial cell according to the method of claim 1;
- administering the generated type H bone endothelial cell to a subject suffering from a bone disease; and
- thereby promoting bone health in the subject.

7. The method of claim 6, wherein promoting bone health comprises one or more bone improvement selected from the group consisting of increasing the amount of bone capillaries or vessels, increasing bone angiogenesis, increasing bone osteogenesis, increasing bone mass, increasing bone formation, promoting bone fracture healing, treating a bone fracture, and treating a bone disorder.

8. The method of claim 6, wherein promoting bone health comprises promoting bone angiogenesis or bone osteogenesis.

9. The method of claim 6, wherein the bone disease is osteoporosis.

10. The method of claim 6, wherein the bone disease is treated by increasing bone angiogenesis.

11. The method of claim 1, wherein the Prolyl-4-hydroxylase inhibitor is cobalt chloride, ciclopirox olamine, L-mimosine, dimethyloxalylglycine, 3,4-dihydoxybenzoate, or (N'-{-5-[Acetyl(hydroxy)amino]pentyl}-N-[5-({4-[(5-aminopentyl)(hydroxy)amino}-4-oxobutanoyl}amino)pentyl]-N-hydroxysuccinamide).

* * * * *